United States Patent
Cho et al.

(10) Patent No.: US 9,727,294 B2
(45) Date of Patent: Aug. 8, 2017

(54) MOBILE DEVICE, SYSTEM AND METHOD FOR MEDICAL IMAGE DISPLAYING USING MULTIPLE MOBILE DEVICES

(71) Applicant: Infinitt Healthcare Co., Ltd., Seoul (KR)

(72) Inventors: Sang Wook Cho, Seoul (KR); Jin Jun Kim, Seoul (KR)

(73) Assignee: Infinitt Healthcare Co., Ltd., Seoul (KR)

( * ) Notice: Subject to any disclaimer, the term of this patent is extended or adjusted under 35 U.S.C. 154(b) by 87 days.

(21) Appl. No.: 14/284,819

(22) Filed: May 22, 2014

(65) Prior Publication Data

US 2014/0347251 A1  Nov. 27, 2014

(30) Foreign Application Priority Data

May 22, 2013 (KR) .................. 10-2013-0057563

(51) Int. Cl.
*G06F 3/14* (2006.01)
*G06F 3/147* (2006.01)
*G06F 19/00* (2011.01)

(52) U.S. Cl.
CPC ............. *G06F 3/14* (2013.01); *G06F 3/147* (2013.01); *G06F 3/1446* (2013.01); *G06F 19/321* (2013.01); *G06F 19/3418* (2013.01); *G06F 3/1454* (2013.01); *G09G 2340/145* (2013.01); *G09G 2354/00* (2013.01); *G09G 2370/042* (2013.01); *G09G 2380/08* (2013.01)

(58) Field of Classification Search
USPC ......................................................... 345/2.3
See application file for complete search history.

(56) References Cited

U.S. PATENT DOCUMENTS

| 8,226,476 B2 | 7/2012 | Haltovsky et al. |
| 8,370,293 B2 | 2/2013 | Iwase et al. |
| 8,789,131 B2 | 7/2014 | Choi et al. |

(Continued)

FOREIGN PATENT DOCUMENTS

| JP | 5523461 B2 | 6/2014 |
| KR | 10-2006-0052726 | 5/2006 |

(Continued)

*Primary Examiner* — Gustavo Polo
(74) *Attorney, Agent, or Firm* — Mintz Levin Cohn Ferris Glovsky and Popeo, P.C.; Kongsik Kim; Jonathon Western

(57) ABSTRACT

A system, mobile device and method for displaying a medical image using multiple mobile devices are disclosed. A master mobile device for displaying a medical image includes a communication unit, a device information collection unit, and an arrangement designation unit. The communication unit wirelessly communicates with surrounding mobile devices and a medical image provision system. The device information collection unit searches for surrounding slave mobile devices that are to operate as slaves via the communication unit, collects the device information of each of the retrieved slave mobile devices while communicating with the retrieved slave mobile devices, and control the communication unit to transmit device information of the master mobile device and the collected device information to the medical image provision system. The arrangement designation unit receives recommended arrangement information from the medical image provision system, and outputs the recommended arrangement information.

10 Claims, 22 Drawing Sheets

(56) References Cited

U.S. PATENT DOCUMENTS

| | | |
|---|---|---|
| 8,868,490 B2 | 10/2014 | Iwase et al. |
| 2006/0116164 A1 | 6/2006 | Kang |
| 2008/0194238 A1 | 8/2008 | Kwon |
| 2011/0109526 A1 | 5/2011 | Bauza et al. |
| 2012/0210349 A1 | 8/2012 | Campana et al. |
| 2015/0006203 A1 | 1/2015 | Iwase et al. |

FOREIGN PATENT DOCUMENTS

| | | |
|---|---|---|
| KR | 10-2006-0052727 | 5/2006 |
| KR | 10-2006-0066630 | 6/2006 |
| KR | 10-0594065 B1 | 6/2006 |
| KR | 10-2011-0082636 A | 7/2011 |
| KR | 10-2011-0125724 | 11/2011 |
| KR | 10-1145936 B1 | 5/2012 |
| KR | 10-2013-0025994 | 3/2013 |

MOBILE DEVICE, SYSTEM AND METHOD FOR MEDICAL IMAGE DISPLAYING USING MULTIPLE MOBILE DEVICES

CROSS-REFERENCE TO RELATED APPLICATION

This application claims under 35 U.S.C. §119(a) the benefit of Korean Application No. 10-2013-0057563 filed on May 22, 2013, which is incorporated herein by reference.

TECHNICAL FIELD

The present invention relates to a method of providing a medical image using multiple mobile devices and, more particularly, to a method of providing a medical image based on based on the characteristics of the medical image and the performance of mobile devices.

BACKGROUND ART

In general, a picture archiving & communication system (PACS) is a system in which the physical regions of patients are imaged via various types of medical equipment and images are transmitted in a digital manner and then read via computers.

A PACS acquires the image information of patients, imaged using various types of imaging equipment, such as a computed tomography (CT) scanner, a magnetic resonance imaging (MRI) scanner, a fluoroscopy machine, a computed tomography angiography (CTA) scanner, etc., in a hospital or a clinic, in a digital form, rather than a film form, stores it in a digital storage medium, and transmits it to terminals over a network, thereby enabling the image information of the patients to be searched, interpreted and used for diagnosis in real time in any place where a terminal is present, such as an examination room, a ward, or the like.

A PACS can improve the convenience of treatment and research because it may be accessed even using a mobile device. However, in a search for a medical image using a mobile device, information that may be searched for at once is inevitably limited due to the limited size of a display and the number of displays.

As an example of conventional multi-screen image display technology, U.S. Patent Application Publication No. 2011-0109526 entitled "Multi-Screen Image Display" was proposed. This preceding technology discloses a technology for controlling the dislocation of an image between a plurality of display panels that occurs because an image of a boundary dimension part between the display panels is not output when an image is split and displayed on the display panels.

Although the conventional multi-screen display technology proposes a display method using a plurality of mobile devices, it does not display a medical image based on the characteristics of the medical image.

Accordingly, there is a need for a method for displaying a medical image using multiple mobile devices based on the characteristics of a medical image and the performance of mobile devices.

SUMMARY OF THE DISCLOSURE

Accordingly, the present invention has been made keeping in mind the above problems occurring in the prior art, and an object of the present invention is to provide a method and system for displaying a medical image using multiple mobile devices.

More particularly, an object of the present invention is to provide technology for providing a medical image using a plurality of mobile devices based on the characteristics of the medical image and the performance of the mobile devices.

Another object of the present invention is to provide technology in which the master mobile device of a system for displaying a medical image searches for surrounding slave mobile devices capable of communication, collects the device information of the retrieved slave mobile devices, transmits the collected device information to a medical image provision system, and outputs recommended arrangement information for the mobile devices when receiving the recommended arrangement information from the medical image provision system, thereby designating the arrangement of the mobile devices.

Yet another object of the present invention is to provide technology that is configured to, when the medical image provision system receives device information about mobile devices, designate the type of medical image to be output to each of the mobile devices based on the device information, designate a layout arrangement, generate recommended arrangement information including the type of designated image and the designated layout arrangement, and transmit the recommended arrangement information to the master mobile device, thereby designating the arrangement of the mobile devices.

Still another object of the present invention is to provide technology that is configured to, in the case where a medical image is split and provided, when the medical image provision system receives device information about mobile devices, to designate an layout arrangement and the regions of the medical image to be output by the mobile devices based on the device information, generate recommended arrangement information including the arrangement information and information about the regions of the medical image assigned to the mobile devices, and transmit the recommended arrangement information to the master mobile device, thereby designating the arrangement of the mobile devices.

In accordance with an aspect of the present invention, there is provided a master mobile device for displaying a medical image, including a communication unit configured to wirelessly communicate with surrounding mobile devices and a medical image provision system; a device information collection unit configured to search for surrounding slave mobile devices that are to operate as slaves via the communication unit; collect device information of each of the retrieved slave mobile devices while communicating with the retrieved slave mobile devices; and control the communication unit to transmit device information of the master mobile device and the collected device information to the medical image provision system; and an arrangement designation unit configured to receive recommended arrangement information for the master mobile device and the retrieved slave mobile devices from the medical image provision system; and output the recommended arrangement information.

The device information may include one or more of the resolution of a display included in each of the mobile devices, the size of the display screen, the contrast ratio of the display screen, the response speed of the display screen, information about whether or not the display screen is capable of outputting a three-dimensional (3D) image, the size of the mobile device, the processing speed of the mobile device, and the remaining storage space of the mobile device.

The recommended arrangement information may include information about identities (IDs) of the master mobile device and the retrieved slave mobile devices; arrangement information about a layout arrangement of the master mobile device and the retrieved slave mobile devices; and information about a type of medical image to be output by each of the master mobile device and the retrieved slave mobile devices.

After outputting the recommended arrangement information, the arrangement designation unit, once the layout arrangement of the master mobile device and the retrieved slave mobile devices has been received from a user or a type of medical image to be output to each of the master mobile device and the retrieved slave mobile devices has been selected by the user, may provide the communication unit, the received layout arrangement or the type of selected image to be transmitted to the medical image provision system via the communication unit.

The master mobile device may further include an image processing unit configured to receive a medical image to be displayed on the master mobile device from the medical image provision system.

The master mobile device may further include an image processing unit configured to receive medical images to be output to the respective slave mobile devices from the medical image provision system and to control the communication unit to transmit the received medical images to the slave mobile devices via the communication unit.

The master mobile device may further include an device interface unit configured to receive input information from each of the slave mobile devices (information inputted by user at the slave mobile devices) and to control the communication unit to transmit the input information is transmitted to the medical image provision system via the communication unit.

The recommended arrangement information, if a single medical image is split and displayed on the master mobile device and the retrieved slave mobile devices, may include information about IDs of the master mobile device and the retrieved slave mobile devices, arrangement information about an layout arrangement of the master mobile device and the retrieved slave mobile devices, and information about regions of the medical image to be output by the master mobile device and the retrieved slave mobile devices.

The arrangement designation unit, if the layout arrangement of the master mobile device and the retrieved slave mobile devices or a change of the region of the medical image to be output by each of the master mobile device and the retrieved slave mobile devices is received from a user after outputting the recommended arrangement information, may control the communication unit to transmit the received layout arrangement or the changed region of the medical image to the medical image provision system via the communication unit.

In accordance with another aspect of the present invention, there is provided a medical image provision system for displaying a medical image using multiple mobile devices, the medical image provision system including a communication unit configured to wirelessly communicate with a plurality of mobile devices; a device information reception unit configured to receive device information of each of a master mobile device and slave mobile devices via the communication unit; and an arrangement unit configured to designate a type of medical image to be output to each of the master mobile device and the slave mobile devices based on the device information of each of the master mobile device and the slave mobile devices; designate a layout arrangement of the master mobile device and the slave mobile devices; generate recommended arrangement information comprising the type of medical image configured for each of the master mobile device and the slave mobile devices and the designated layout arrangement; and control the communication unit to transmit the recommended arrangement information to the master mobile device via the communication unit.

The medical image provision system may further include an image processing unit configured to send the medical images to be output by the master mobile device and the slave mobile devices to the master mobile device; receive input information, received from the master mobile device or each of the slave mobile devices, to the master mobile device; determine a mobile device whose medical image to be output is changed based on the input information; and control the communication unit to transmit the changed medical image of the determined mobile device to the master mobile device via the communication unit.

The medical image provision system may further include an image processing unit configured to send the medical images to be output by the master mobile device and the slave mobile devices to the master mobile device and the slave mobile devices; receive input information from the master mobile device or each of the slave mobile devices; determine a mobile device whose medical image to be output is changed based on the input information; and control the communication unit to transmit the changed medical image to the determined mobile device via the communication unit.

The arrangement unit may set the layout arrangement of the master mobile device and the slave mobile devices to one or more of an layout arrangement predetermined by a user, an layout arrangement configured most frequently, and an layout arrangement predetermined based on the user's role.

In accordance with another aspect of the present invention, there is provided a medical image provision system for displaying a medical image using multiple mobile devices, the medical image provision system including a communication unit configured to wirelessly communicate with a plurality of mobile devices; a device information reception unit configured to receive device information of each of a master mobile device and slave mobile devices via the communication unit; and an arrangement unit configured to, if the medical image is split and displayed, designate an layout arrangement of the master mobile device and the slave mobile devices and regions of a medical image to be output by the master mobile device and retrieved slave mobile devices based on the device information of each of the master mobile device and the slave mobile devices; generate recommended arrangement information comprising the layout arrangement and information about the regions of the medical image configured for the master mobile device and the retrieved slave mobile devices; and control the communication unit to transmit the recommended arrangement information to the master mobile device via the communication unit.

The arrangement unit may be further configured to determine a part of interest in annotation, marking, or a header included in the medical image; and designate the layout arrangement so that the part of interest is placed in a mobile device having a highest resolution or a mobile device having a largest display.

The medical image provision system may further include an image processing unit configured to send the medical images to be output by the master mobile device and the slave mobile devices to the master mobile device; receive input information, received from the master mobile device or each of the slave mobile devices, to the master mobile device; determine a mobile device whose medical image to be output is changed based on the input information; and control the communication unit to transmit the changed medical image of the determined mobile device to the master mobile device via the communication unit.

The medical image provision system may further include an image processing unit configured to send the medical images to be output by the master mobile device and the slave mobile devices to the master mobile device and the slave mobile devices; receive input information from the master mobile device or each of the slave mobile devices; determine a mobile device whose medical image to be output is changed based on the input information; and control the communication unit to transmit the changed medical image to the determined mobile device via the communication unit.

In accordance with still another aspect of the present invention, there is provided a method of displaying a medical image in a master mobile device of a system for displaying medical image, the method including searching for surrounding slave mobile devices capable of communication; collecting the device information of each of the retrieved slave mobile devices while communicating with the retrieved slave mobile devices; sending device information of the master mobile device and the collected device information to a medical image provision system; receiving recommended arrangement information for the master mobile device and the retrieved slave mobile devices from the medical image provision system; and outputting the recommended arrangement information.

The recommended arrangement information may include information about identities (IDs) of the master mobile device and the retrieved slave mobile devices; arrangement information about a layout arrangement of the master mobile device and the retrieved slave mobile devices; and information about a type of medical image to be output by each of the master mobile device and the retrieved slave mobile devices.

The recommended arrangement information, if a single medical image is split and displayed on the master mobile device and the retrieved slave mobile devices, may include information about IDs of the master mobile device and the retrieved slave mobile devices, arrangement information about a layout arrangement of the master mobile device and the retrieved slave mobile devices, and information about regions of the medical image to be output by the master mobile device and the retrieved slave mobile devices.

In accordance with still another aspect of the present invention, there is provided a method of providing medical images from a medical image provision system to display on a plurality of mobile devices, the method including receiving device information of each of a master mobile device and slave mobile devices; designating the type of medical image to be output to each of the master mobile device and the slave mobile devices based on the device information of each of the master mobile device and the slave mobile devices; designating the layout arrangement of the master mobile device and the slave mobile devices; generating recommended arrangement information comprising the type of image configured for each of the master mobile device and the slave mobile devices and the designated layout arrangement; and sending the recommended arrangement information to the master mobile device.

Designating the layout arrangement of the master mobile device and the slave mobile devices may include setting the layout arrangement of the master mobile device and the slave mobile devices as one or more of an layout arrangement predetermined by a user, an layout arrangement configured most frequently, and an layout arrangement predetermined based on the user's role.

In accordance with still another aspect of the present invention, there is provided a method of providing medical images from a medical image provision system to display on a plurality of mobile devices, the method including receiving device information of each of a master mobile device and slave mobile devices; if the medical image is split and displayed, designating a layout arrangement of the master mobile device and the slave mobile devices and regions of a medical image to be output by the master mobile device and retrieved slave mobile devices based on the device information of each of the master mobile device and the slave mobile devices; generating recommended arrangement information comprising the layout arrangement and information about the regions of the medical image configured for the master mobile device and the retrieved slave mobile devices; and sending the recommended arrangement information to the master mobile device via the communication unit.

Designating the layout arrangement and the regions of the medical image to be output may include determining a part of interest in annotation, marking, or a header included in the medical image; and designating the layout arrangement so that the part of interest is placed in a mobile device having a highest resolution or a mobile device having a largest display.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Figure 1:
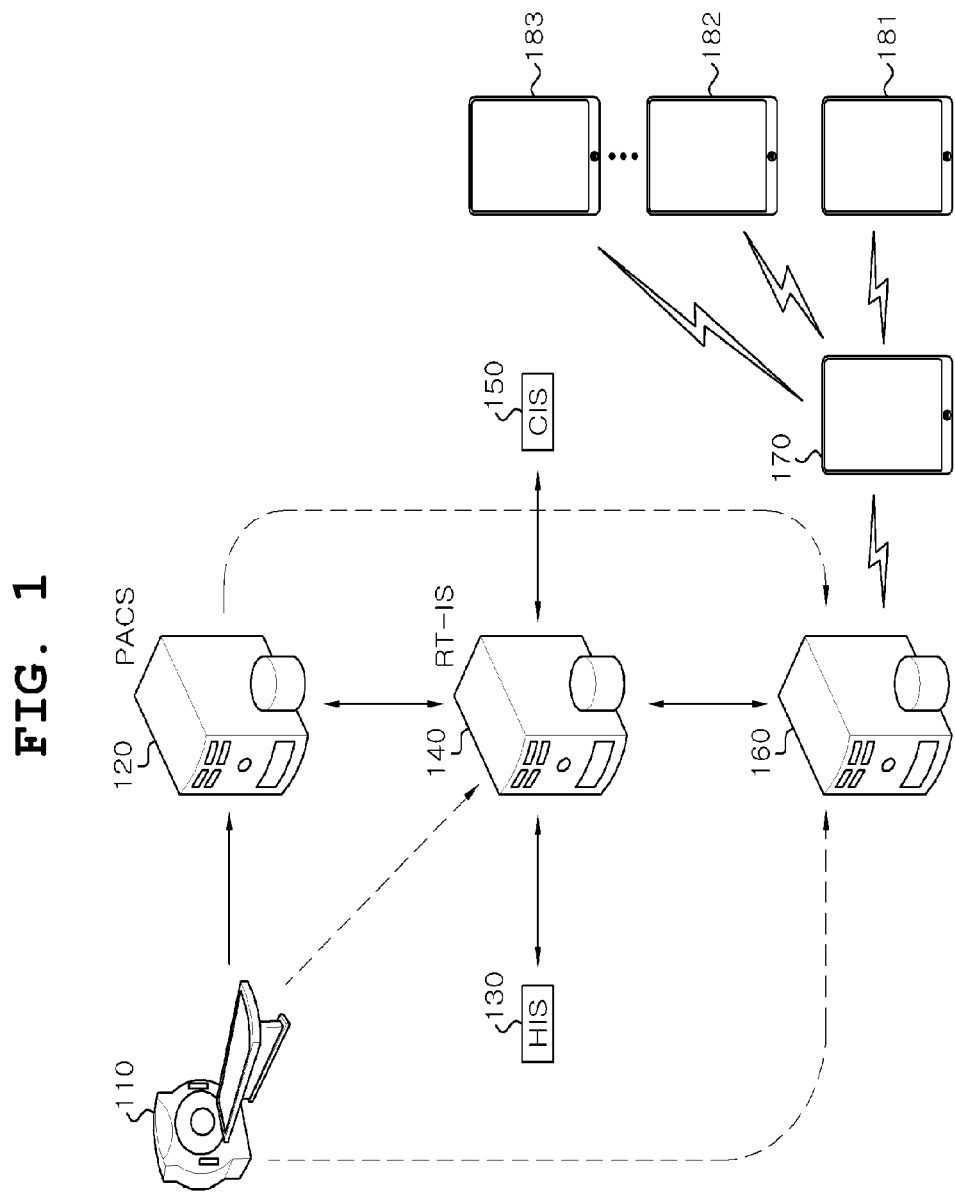
FIG. 1 is a diagram illustrating the schematic configuration of a system for displaying a medical image using multiple mobile devices according to an embodiment of the present invention.

Hereinafter, embodiments of the present invention will be described in detail with reference to the accompanying drawings. Reference now should be made to the elements of drawings, in which the same reference numerals are used throughout the different drawings to designate the same elements. In the following description, detailed descriptions of known elements or functions that may unnecessarily make the gist of the present invention obscure will be omitted.

A method and system for displaying a medical image using multiple mobile devices according to embodiments of the present invention are described in detail below with reference to FIGS. 1 to 22.

FIG. 1 is a diagram illustrating the schematic configuration of the system for displaying a medical image using multiple mobile devices according to an embodiment of the present invention.

Referring to FIG. 1, the system for displaying a medical image according to an embodiment of the present invention may include a medical imaging apparatus 110, a PACS 120, a hospital information system (HIS) 130, an RT information management server (RT-IS) 140, a CIS 150, a medical image provision system 160, a master mobile device 170, and slave mobile devices 181, 182 and 183.

The medical imaging apparatus 110 is an apparatus configured to obtain a medical image of a patient. The medical imaging apparatus 110 photographs a medical image of a patient, converts the a medical image into images in a digital imaging and communications in medicine (DICOM) format or a non-DICOM format, and provides the digital images to one or more of the PACS 120, the RT-IS 140, and the medical image provision system 160.

In this case, the medical imaging apparatus 110 may include computed tomography (CT) equipment, magnetic resonance imaging (MRI) equipment, positron emission tomography (PET) equipment, a CT simulator, and computed radiography (CR) equipment.

The PACS 120 stores a medical image, received from the medical imaging apparatus 110, in the DICOM format, and transfers the stored medical image to a device or a system that requests the medical image.

In this case, the PACS 120 may transfer the medical image to one or more of the RT-IS 140 and the medical image provision system 160.

The HIS 130 is a system in which the overall management business of a hospital has been computerized and automated. The HIS 130 manages and transfers all data within a hospital, such as the registration of patients, treatment, and receipt, and efficiently manages all administrative procedures in the hospital.

In this case, the HIS 130 may manage and transfer data while operating in conjunction with an outpatient clinic substation (OCS) and an electronic medical record (EMR) system.

The CIS 150 is a digital medical system configured to store bio signals and data, generated by electrocardiogram (ECG) equipment and common outpatient test equipment, in a digital form and to help the bio signals and data to be searched for and diagnosed over a network.

The RT-IS 140 is a server configured to store and manage information related to radiation treatment (RT). The RT-IS 140 stores medical images of a patient for generating RT plan data, the past RT plan data of the patient, RT result data based on the RT plan data, a statistical model based on the RT result data, and the personalized data of the patient.

In this case, the RT-IS 140 may collect and store the personalized data of the patient while operating in conjunction with the HIS 130 and the CIS 150, and may store predetermined RT plan data. The statistical model may be a statistical model for a change of RT plan data that has been generated based on the changed data of RT plan data collected in association with RT result data. Such a statistical model may be generated by the RT-IS 140, or may be generated by separate equipment and stored in the RT-IS 140.

The medical image provision system 160 may provide various types of medical images or medical information to the mobile devices 170, 181, 182 and 183, or may split a single medical image and provide the split medical images to the mobile devices 170, 181, 182 and 183, through wireless communication with the master mobile device 170 and the slave mobile devices 181, 182 and 183.

The medical image provision system 160 needs to designate the arrangement of the mobile devices 170, 181, 182 and 183 prior to the provision of a medical image. When designating the arrangement of the mobile devices 170, 181, 182 and 183, the medical image provision system 160 configures the arrangement based on the characteristics of the medical image and the device characteristics of the mobile devices 170, 181, 182 and 183.

Although in FIG. 1, the medical image provision system 160 has been illustrated as being separate from the PACS 12, the medical image provision system 160 may be included in the PACS 120 in an embodiment of the present invention.

Furthermore, according to an embodiment of the present invention, the medical image provision system 160 may be included in the server of the PACS 120.

Figure 2:
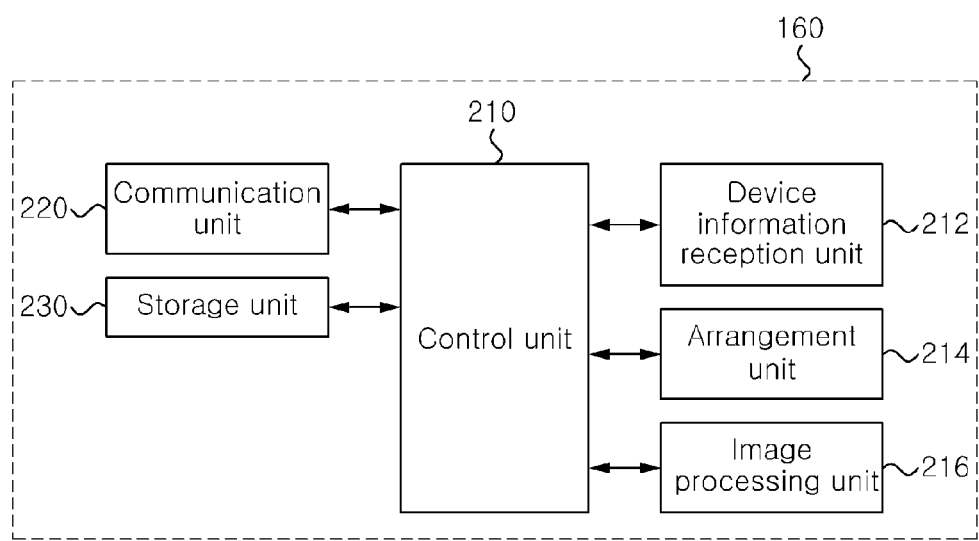
FIG. 2 is a diagram illustrating the configuration of a medical image provision system according to an embodiment of the present invention.

FIG. 2 is a diagram illustrating the configuration of the medical image provision apparatus according to an embodiment of the present invention.

Referring to FIG. 2, the medical image provision system 160 may be implemented as a computing system including a control unit 210, a device information reception unit 212, an arrangement unit 214, an image processing unit 216, a communication unit 220, and a storage unit 230. The control unit 210, the device information reception unit 212, the arrangement unit 214, and the image processing unit 216 may be implemented in at least one processor in the computing system 160.

The communication unit 220 may include a receiver and a transmitter. The communication unit 220 may be connected to the plurality of mobile devices 170, 181, 182 and 183 through wireless communication, and may be configured to send and receive data to and from the plurality of mobile devices 170, 181, 182 and 183. In this case, the communication unit 220 may use short-distance communication. Available short-distance wireless communication may include Wi-Fi, Bluetooth, near field communication (NFC), and infrared communication.

The storage unit 230 may store an operating system operative to control the overall operation of the medical image provision system 160, an application program and data (e.g., a medical image and medical information), and may store the device information of the plurality of mobile devices 170, 181, 182 and 183 that is received via the communication unit 220 according to an embodiment of the present invention, and recommended arrangement information set by the arrangement unit 214 or arrangement information, that is, information about the arrangement of the mobile devices 170, 181, 182 and 183 set by a user and received via the communication unit 220. The storage unit 230 may be a storage device such as a flash memory or a hard disk drive, etc.

The device information reception unit 212 may be implemented as a sub-module of a processor in the computing system 160 and may receive the device information of each of the master mobile device 170 and the slave mobile devices 181, 182 and 183 that belong to the plurality of mobile devices 170, 181, 182 and 183 is received via the communication unit 220. In this case, the device information may include one or more of the resolution of a display included in each mobile device, the size of the display, the contrast ratio of the display, the response speed of the display, information about whether the display is capable of outputting a 3D image, the size of the mobile device, the processing speed of the mobile device, and the remaining storage space of the mobile device.

The arrangement unit 214 may also be implemented as another sub-module of the processor in the computing system 160, may designate the type of medical image to be output to each of the master mobile device 170 and the slave mobile devices 181, 182 and 183 based on based on the device information of each of the master mobile device 170 and the slave mobile devices 181, 182 and 183, may designate the layout arrangement of the master mobile device 170 and the slave mobile devices 181, 182 and 183, may generate recommended arrangement information including the type of medical image configured in each of the master mobile device 170 and the slave mobile devices 181, 182 and 183 and a designated layout arrangement, and provide the recommended arrangement information to be transmitted to the master mobile device 170 via the communication unit 220.

For example, if the type of medical image requires high resolution for reading, the arrangement unit 214 may make a configuration so that the medical image is placed in a mobile device that belongs to the mobile devices 170, 181, 182 and 183 and that has the highest resolution. In this case, if the type of medical image requires high resolution, the arrangement unit 214 may make a configuration so that the medical image is placed in a mobile device that belongs to mobile devices having high resolution, that has high processing speed, and that has substantial storage space because the amount of received data is large.

Furthermore, if the type of medical image is a three-dimensional (3D) image, the arrangement unit 214 may make a configuration so that the medical image is placed in a mobile device that belongs to the mobile devices 170, 181, 182 and 183 and that is capable of displaying a 3D image.

In this case, the type of medical image to be output may include a medical image captured using photographing equipment, such as CT equipment or MRI equipment, a 3D medical image rendered in a 3D way, a medical image displaying an affected part, a coronal medical image, a sagittal medical image, and a horizontal medical image. The type of medical image to be output may further include medical information in addition to a medical image. In this case, the medical information may include a worklist, medical records, patient information, and a medical plan.

The arrangement unit 214 may set the layout arrangement of the master mobile device 170 and the slave mobile devices 181, 182 and 183 to one or more of an layout arrangement predetermined by a user, an layout arrangement designated most frequently, and an layout arrangement predetermined based on a user's role. In this case, the role of the user may include one or more of a radiologist, a clinician, a technician, and a transcriber.

If a medical image is split and provided to the mobile devices 170, 181, 182 and 183, the arrangement unit 214 may designate the layout arrangement of the master mobile device 170 and the slave mobile devices 181, 182 and 183 and the region of a medical image to be output by each of the master mobile device 170 and retrieved slave mobile devices 181, 182 and 183 based on the device information of each of the master mobile device 170 and the slave mobile devices 181, 182 and 183, may generate recommended arrangement information including the layout arrangement and information about the region of the medical image configured for each of the master mobile device 170 and retrieved slave mobile devices (e.g., 181, 182 and 183), and may control the communication unit 220 so that the recommended arrangement information is transmitted to the master mobile device 170 via the communication unit 220.

In this case, if the medical image is split and provided to the mobile devices 170, 181, 182 and 183, the arrangement unit 214 may check annotation, marking or the part of interest of a header included in the medical image, may check the location of the part of interest in the medical image, and may designate the layout arrangement so that the part of interest of the medical image is placed in a mobile device having the highest resolution or a mobile device having the largest display.

The image processing unit 216 may also be implemented as another sub-module of the processor in the computing system 160, may send medical images to the master mobile device 170 and the slave mobile devices 181, 182 and 183 from which the medical images will be output, may receive input information from the master mobile device 170 or each of the slave mobile devices 181, 182 and 183, may determine a mobile device whose medical image to be output is changed based on the input information, and may control the communication unit 220 so that the changed medical image is transmitted to the checked mobile device via the communication unit 220.

In this case, the input information may include information for selecting part of a medical image, information for enlarging or reducing a medical image, information for inputting writing or figures to a medical image, information for marking a specific area of a medical image, and information for executing a specific application on a medical image.

The image processing unit 216 may send medical images to be output by the master mobile device 170 and the slave mobile devices 181, 182 and 183 to the master mobile device 170, may receive input information received by the master mobile device 170 or the slave mobile devices 181, 182 and 183 from the master mobile device 170, may determine a mobile device whose medical image to be output is changed based on the input information, and may control the communication unit 220 so that the changed medical image of the checked mobile device is transmitted to the master mobile device 170 via the communication unit 220.

The control unit 210 may control the overall operation of the medical image provision system 160. Furthermore, the control unit 210 may perform the functions of the device information reception unit 212, the arrangement unit 214 and the image processing unit 216. The control unit 210, the device information reception unit 212, the arrangement unit 214 and the image processing unit 216 have been illustrated as being separate in order to separately describe the functions. Accordingly, the control unit 210, the device information reception unit 212, the arrangement unit 214 and the image processing unit 216 may be implemented in a processor in the medical image provision system 160. Alternatively, the control unit 210 may include at least one processor configured to perform part of the functions of the device information reception unit 212, the arrangement unit 214 and the image processing unit 216.

Figure 3:
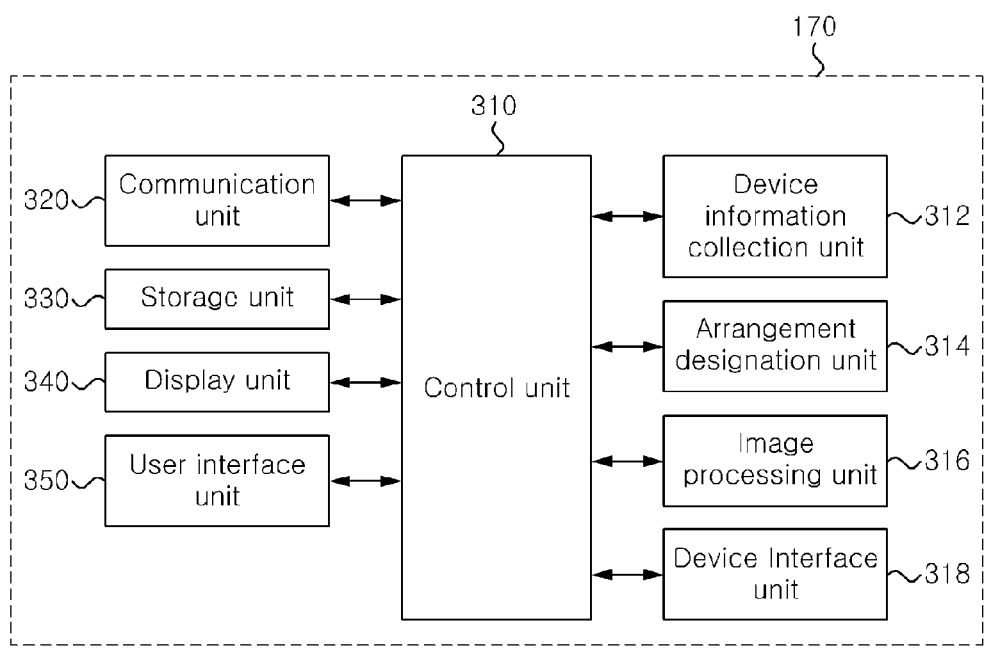
FIG. 3 is a diagram illustrating the configuration of a master mobile device according to an embodiment of the present invention.

FIG. 3 is a diagram illustrating the configuration of the master mobile device according to an embodiment of the present invention.

Referring to FIG. 3, the master mobile device 170 may include a control unit 310, a device information collection unit 312, an arrangement designation unit 314, an image processing unit 316, an device interface unit 318, a communication unit 320, a storage unit 330, a display unit 340, and an user interface unit 350. The control unit 310, the device information collection unit 312, the arrangement designation unit 314, the image processing unit 316, and the device interface unit 318 may be implemented as at least one processor in the master mobile device 170.

The communication unit 320 is a communication interface device including a receiver and a transmitter, and is configured to send and receive data through wireless communication with surrounding mobile devices (e.g., 181, 182 and 183) and the medical image provision system 160. In this case, the communication unit 320 may use short-distance communication. Available short-distance wireless communication may include Wi-Fi, Bluetooth, NFC, and infrared communication. Among them, Bluetooth or Wi-Fi may be preferably used because they are most widely applied to mobile terminals and provide the widest coverage.

The storage unit 330 may store an operating system for controlling the overall operation of the master mobile device 170, an application program, and data (e.g., telephone numbers, SMS messages, compressed image files, and moving images), and may also store the device information of the master mobile device 170 according to an embodiment of the present invention, the pieces of device information of the slave mobile devices 181, 182 and 183 which are received via the communication unit 320, recommended arrangement information received via the communication unit 320, and arrangement information changed by the arrangement designation unit 314. The storage unit 330 may be a storage device including flash memory or a hard disk drive.

The display unit 340 may display information input by a user or information provided to the various menus of the master mobile device 170, and recommended arrangement information, medical images and medical information received from the medical image provision system 160. The display unit 340 may be formed of a liquid crystal display (LCD), organic light emitting diodes (OLEDs), or active matrix organic light emitting diodes (AMOLEDs), but is not limited thereto. If the display unit 340 is formed of a touch screen, the display unit 340 may function as the user interface unit 350.

The user interface unit 350 receives input from the user of the master mobile device 170, and provides the input to the control unit 310. In particular, the user interface unit 350 may receive a change of recommended arrangement information, a change of a medical image, or a change of medical information. Various input devices may be used as the user interface unit 350. For example, the user interface unit 350 may include numerical keys 0~9, text keys, navigator keys, and a plurality of function keys. The user interface unit 350 may be formed of a keypad configured to provide key input data, corresponding to a key pressed by a user, to the control unit 310, or may be formed of a touch screen including a touch sensor for detecting a touch location on a display screen as input.

The device information collection unit 312 may be a sub-module of a processor in the master mobile device 170, may search for surrounding slave mobile devices (e.g., 181, 182 and 183) that will operate as slaves via the communication unit 320, may collect the device information of the retrieved slave mobile devices 181, 182 and 183 through communication with the retrieved slave mobile devices 181, 182 and 183, and may control the communication unit 320 so that the device information of the master mobile device 170 stored in the storage unit 330 and the collected device information of the slave mobile devices 181, 182 and 183 are transmitted to the medical image provision system 160.

In this case, the device information may include one or more of the resolution of a display included in each retrieved mobile device, the size of the display, the contrast ratio of the display, the response speed of the display, information about whether or not the display is able to output a 3D image, the size of the mobile device, the processing speed of the mobile device, and the remaining storage space of the mobile device.

The arrangement designation unit 314 may be another sub-module of the processor in the master mobile device 170, may receive recommended arrangement information for the master mobile device 170 and retrieved slave mobile devices (e.g., 181, 182 and 183) from the medical image provision system 160, and may output the recommended arrangement information to the display unit 340.

In this case, the recommended arrangement information may include information about the IDs of the master mobile device 170 and the retrieved slave mobile devices 181, 182 and 183, arrangement information about the layout arrangement of the master mobile device 170 and the retrieved slave mobile devices 181, 182 and 183, and information about the type of medical image to be output by each of the master mobile device 170 and the retrieved slave mobile devices 181, 182 and 183.

Figure 15:
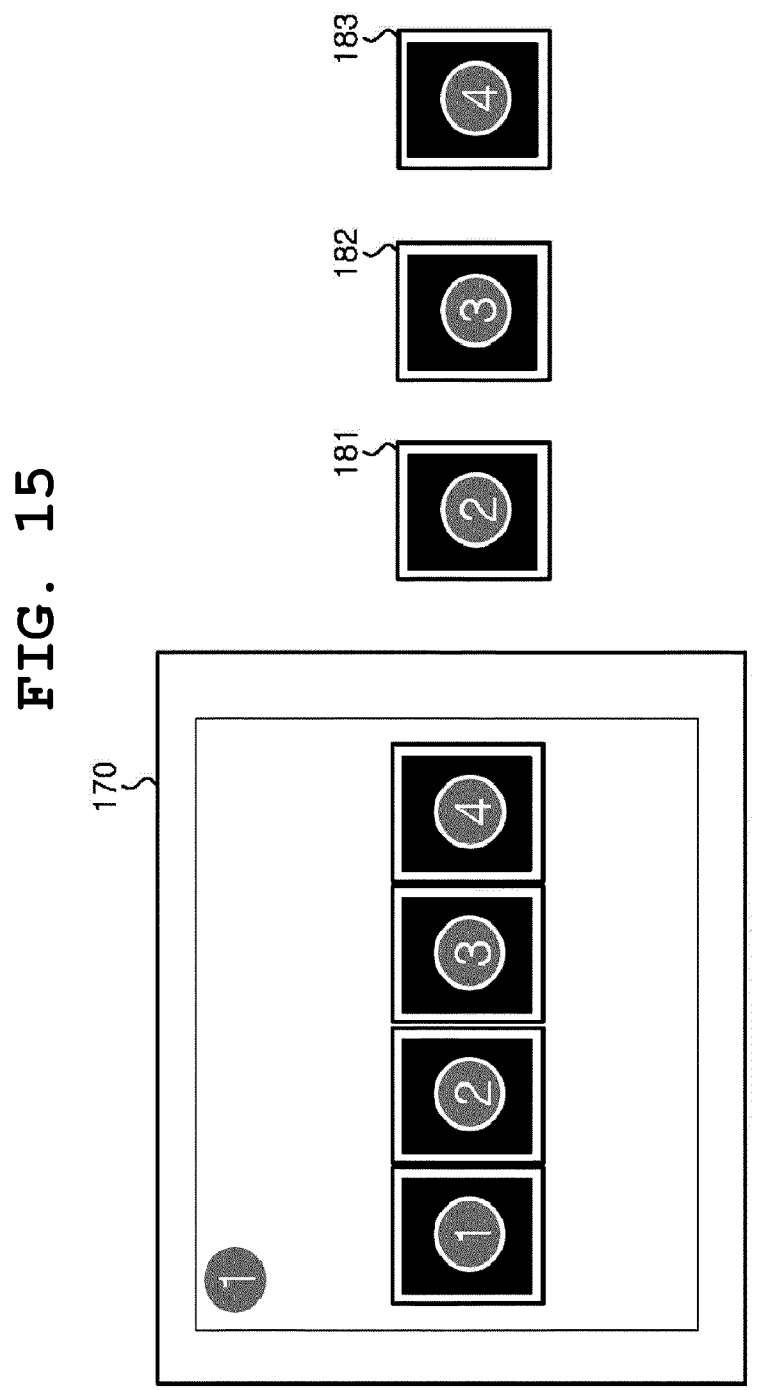
FIG. 15 is a diagram illustrating an example of a configuration screen that is output when the arrangement of the master mobile device and the slave mobile devices is configured according to an embodiment of the present invention.

FIG. 15 is a diagram illustrating an example of a configuration screen that is output when the arrangement of the master mobile device and the slave mobile devices is configured according to an embodiment of the present invention.

Referring to FIG. 15, the arrangement designation unit 314 may output information about the ID of the master mobile device 170 on the left top, and may output the layout arrangement of the mobile devices 170, 181, 182 and 183 and information about the IDs of the respective mobile devices 170, 181, 182 and 183.

In this case, the slave mobile devices 181, 182 and 183 output respective pieces of ID information.

Figure 16:
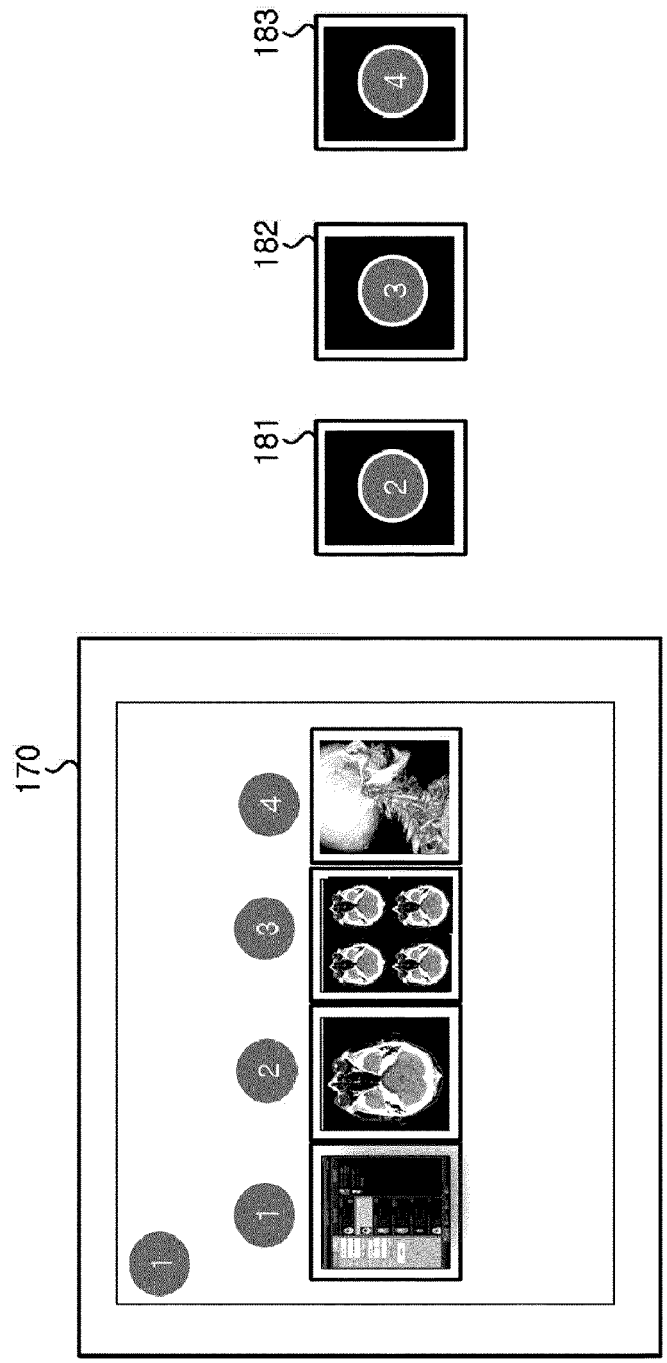
FIG. 16 is a diagram illustrating another example of a configuration screen that is output when the arrangement of the master mobile device and the slave mobile devices is configured according to an embodiment of the present invention.

FIG. 16 is a diagram illustrating another example of a configuration screen that is output when the arrangement of the master mobile device and the slave mobile devices is configured according to an embodiment of the present invention.

Referring to FIG. 16, the arrangement designation unit 314 may output information about the ID of the master mobile device 170 on the left top, and may output the layout arrangement of the mobile devices 170, 181, 182 and 183, information about the IDs of the respective mobile devices 170, 181, 182 and 183, and sample images indicative of the types of medical images to be output by the respective mobile devices 170, 181, 182 and 183.

In this case, the slave mobile devices 181, 182 and 183 output respective pieces of ID information.

Referring back to FIG. 3, if the layout arrangement of the master mobile device 170 and the retrieved slave mobile devices (e.g., 181, 182 and 183) is received from a user or the type of medical image to be output to each of the master mobile device 170 and the retrieved slave mobile devices 181, 182 and 183 is selected by the user after recommended arrangement information has been output, the arrangement designation unit 314 may control the communication unit 320 so that the received layout arrangement or the type of selected image is transmitted to the medical image provision system 160 via the communication unit 320.

Figure 17:
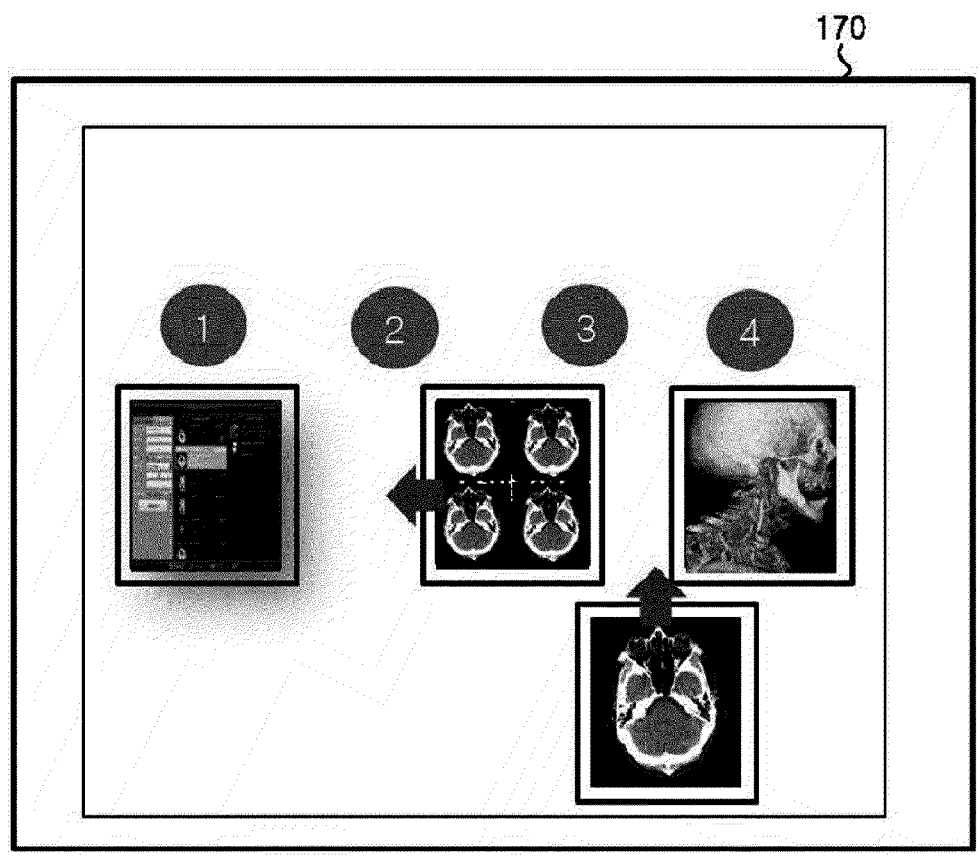
FIG. 17 is a diagram illustrating an example in which the arrangement of the master mobile device and the slave mobile devices is changed according to an embodiment of the present invention.

FIG. 17 is a diagram illustrating an example in which the arrangement of the master mobile device and the slave mobile devices is changed according to an embodiment of the present invention.

Referring to FIG. 17, when a user drags a sample indicative of the type of medical image to be output by the mobile device 181 having the ID information "2" and drops the sample between the mobile device 182 having the ID information "3" and the mobile device 183 having the ID information "4," the arrangement designation unit 314 may detect a user input operative to interchange the type of medical image to be output by the mobile device 181 having the ID information "2" and the type of medical image to be output by the mobile device 182 having the ID information "3" with each other. Furthermore, the arrangement designation unit 314 may provide the changed information to be transmitted to the medical image provision system 160 via the communication unit 320.

Figure 18:
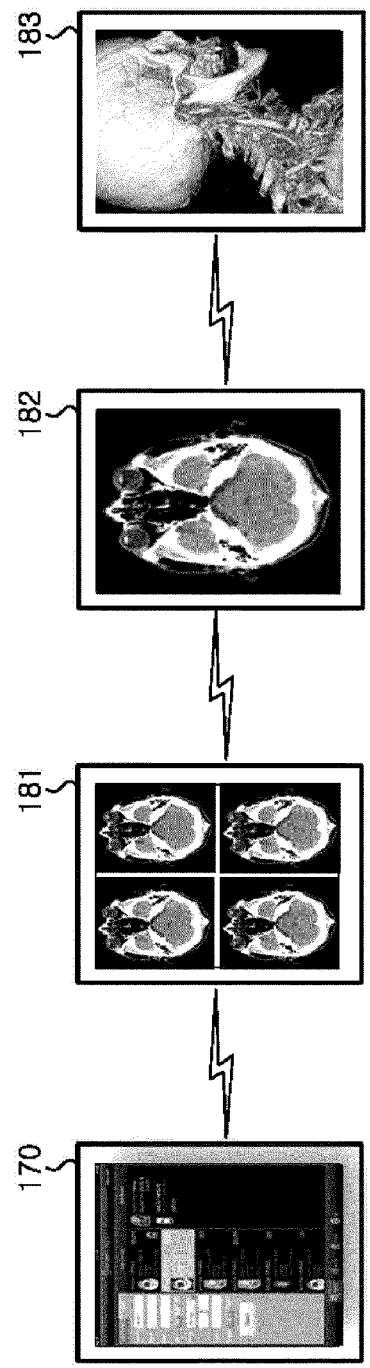
FIG. 18 is a diagram illustrating an example in which a medical image is provided via the master mobile device and the slave mobile devices according to an embodiment of the present invention.

FIG. 18 is a diagram illustrating an example in which a medical image is provided via the master mobile device and the slave mobile devices according to an embodiment of the present invention.

Referring to FIG. 18, once the configuration of an arrangement of the mobile devices 170, 181, 182 and 183 has been completed, as illustrated in FIG. 17, the mobile devices 170, 181, 182 and 183 output received medical images.

If a single medical image is split and displayed on the master mobile device 170 and the retrieved slave mobile devices 181, 182 and 183, the recommended arrangement information may include information about the IDs of the master mobile device 170 and the retrieved slave mobile devices 181, 182 and 183, arrangement information about the layout arrangement of the master mobile device 170 and the retrieved slave mobile devices 181, 182 and 183, and information about the regions of a medical image to be output by the master mobile device 170 and the retrieved slave mobile devices 181, 182 and 183.

Figure 19:
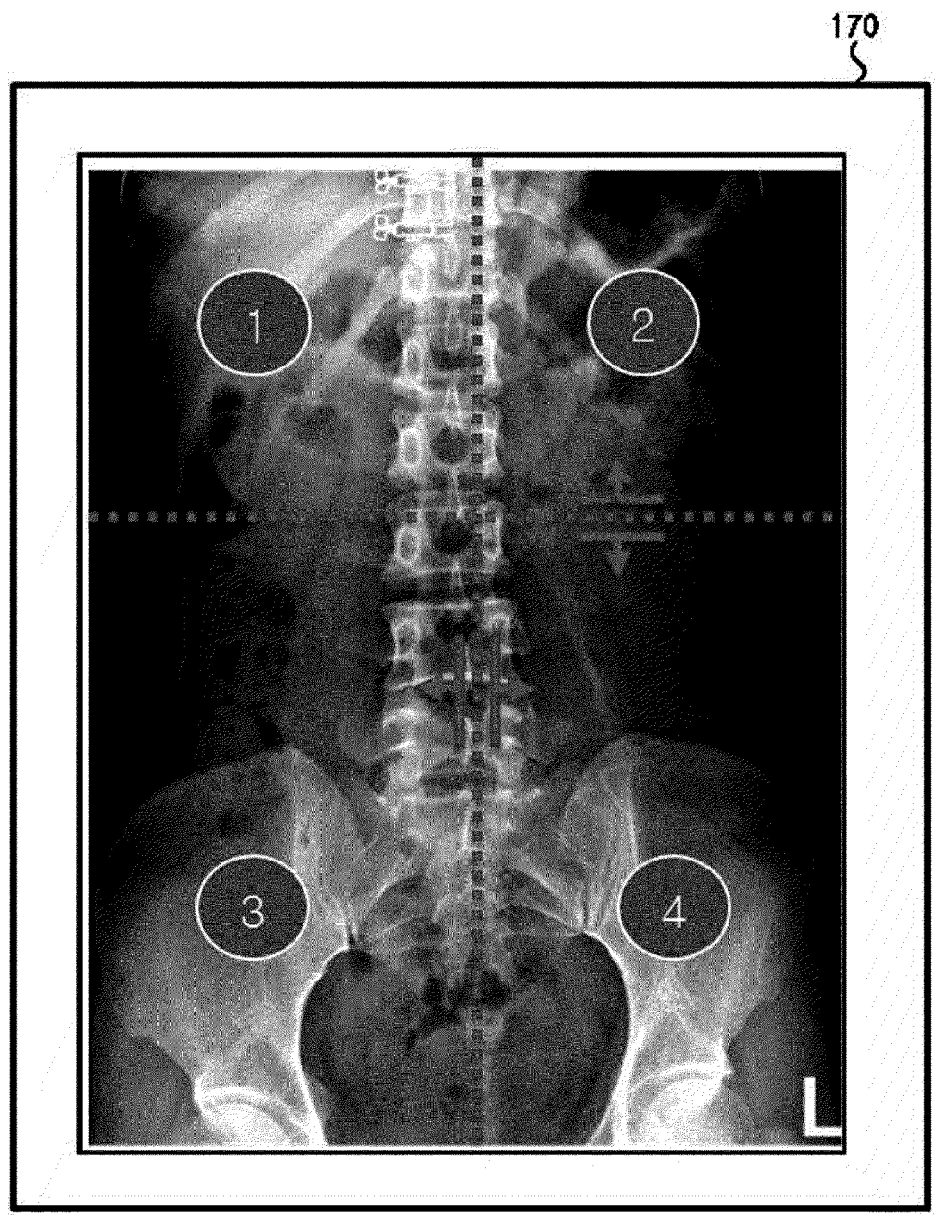
FIG. 19 is a diagram illustrating an example in which the arrangement of the master mobile device and the slave mobile devices is configured when a medical image is split according to an embodiment of the present invention.

FIG. 19 is a diagram illustrating an example in which the arrangement of the master mobile device and the slave mobile devices is configured when a medical image is split according to an embodiment of the present invention.

Referring to FIG. 19, if arrangement information included in received recommended arrangement information is indicative of an layout arrangement in which a single medical image is split in a 2×2 form, the arrangement designation unit 314 outputs the medical image split in the 2×2 form, and indicates mobile devices that will output the split regions of the medical image by indicating information about the IDs of the mobile devices 170, 181, 182 and 183 that are assigned to the respective split regions.

Furthermore, the arrangement designation unit 314 indicates a reference based on which the medical image is split as a dotted line (i.e., a chain double-dashed line) as in the example of FIG. 19, and determines that an input for moving the dotted line is an input for changing a region to be output when the input is detected.

Figure 20:
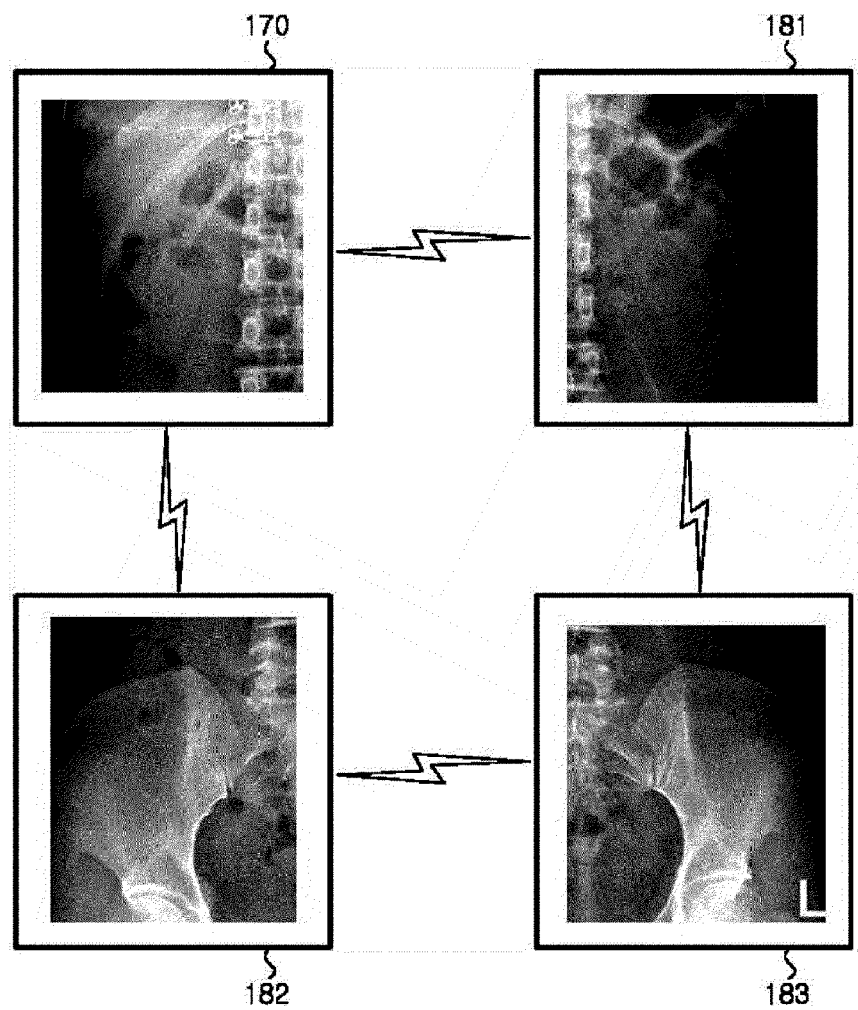
FIG. 20 is a diagram illustrating the case where the medical image configured in FIG. 19 is output via the master mobile device and the slave mobile devices.

FIG. 20 is a diagram illustrating the case where the medical image configured in FIG. 19 is output via the master mobile device and the slave mobile devices.

Referring to FIG. 20, once the configuration of an arrangement of the mobile devices 170, 181, 182 and 183 has been completed, as illustrated in FIG. 19, the medical image is received, and the regions of the medical image to be output by the respective mobile devices 170, 181, 182 and 183 are output.

Figure 21:
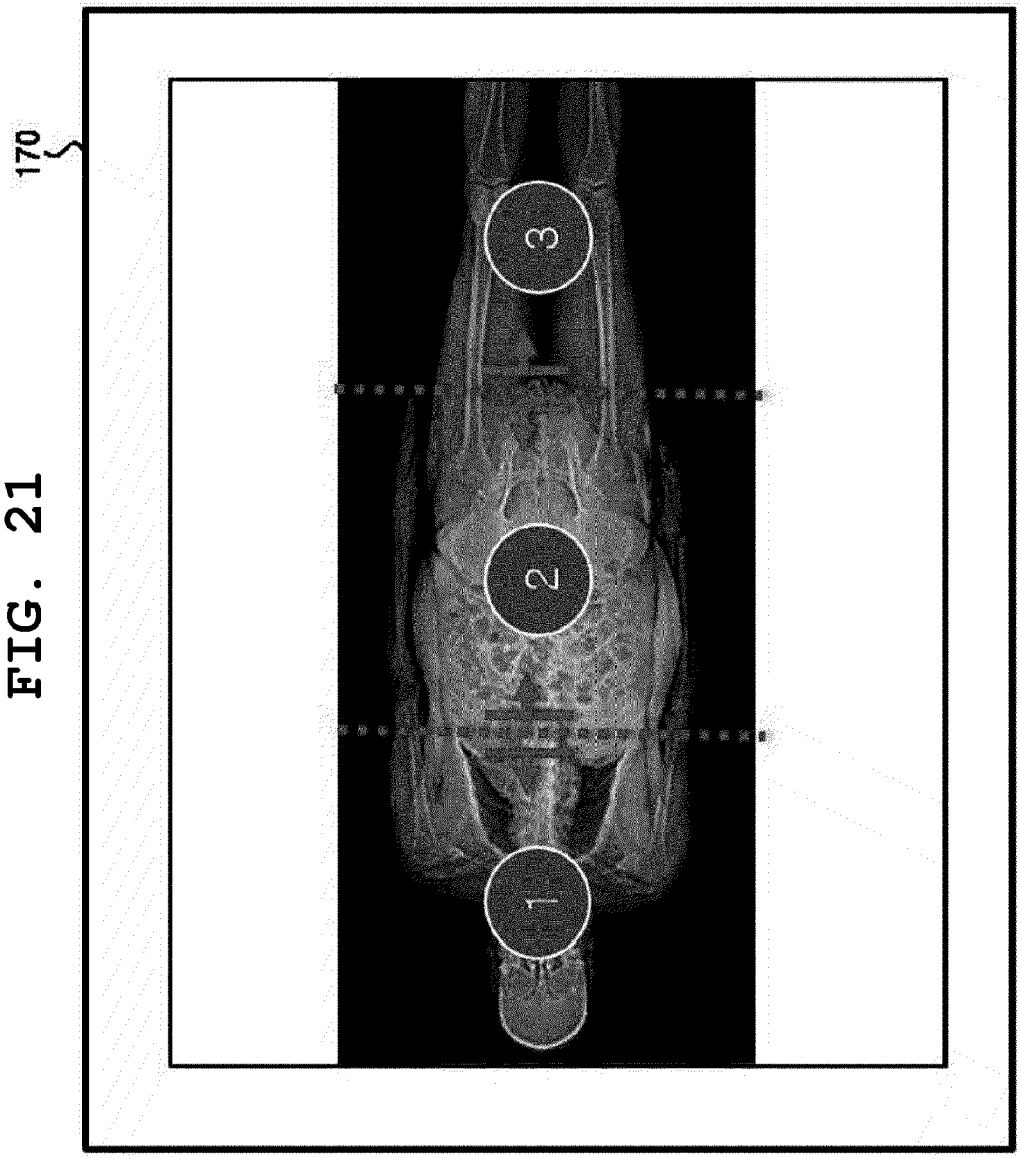
FIG. 21 is a diagram illustrating another example in which the arrangement of the master mobile device and the slave mobile devices is configured when a medical image is split according to an embodiment of the present invention.

FIG. 21 is a diagram illustrating another example in which the arrangement of the master mobile device and the slave mobile devices is configured when a medical image is split according to an embodiment of the present invention.

Referring to FIG. 21, if arrangement information included in received recommended arrangement information is indicative of an layout arrangement in which a single medical image is split in a 1×3 form, the arrangement designation unit 314 outputs the medical image split in the 1×3 form and indicates mobile devices that will output the split regions of the medical image by indicating information about the IDs of the mobile devices 170, 181, 182 and 183 that are assigned to the respective split regions.

Furthermore, the arrangement designation unit 314 indicates a reference based on which the medical image is split as a dotted line (i.e., a chain double-dashed line) as in the example of FIG. 21, and determines that an input for moving the dotted line is an input for changing a region to be output when the input is detected.

Figure 22:
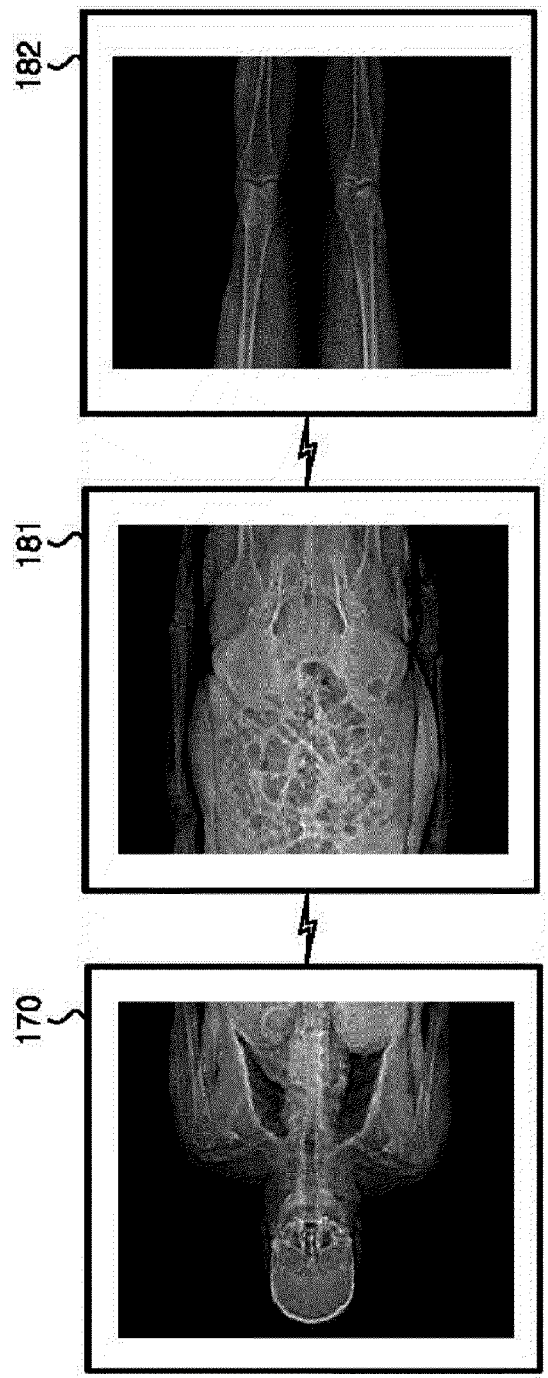
FIG. 22 is a diagram illustrating the case where the medical image configured in FIG. 20 is output via the master mobile device and the slave mobile devices.

FIG. 22 is a diagram illustrating the case where the medical image configured in FIG. 20 is output via the master mobile device and the slave mobile devices.

Referring to FIG. 22, once the configuration of an arrangement of the mobile devices 170, 181, 182 and 183 has been completed, as illustrated in FIG. 21, the medical image is received, and the regions of the medical image to be output by the respective mobile devices 170, 181, 182 and 183 are output.

Referring back to FIG. 3, when the layout arrangement of the master mobile device 170 and retrieved slave mobile devices (e.g., 181, 182 and 183) or a change of the regions of the medical image to be output by the master mobile device 170 and the retrieved slave mobile devices 181, 182 and 183, respectively, is received from a user after the output of recommended arrangement information if a medical image is split and provided to the mobile devices 170, 181, 182 and 183, the arrangement designation unit 314 may control the communication unit 320 so that the received layout arrangement or the changed regions of the medical image are transmitted to the medical image provision system 160 via the communication unit 320.

The image processing unit 316 may be another sub-module of the processor in the master mobile device 170, may receive a medical image to be output to/displayed on the master mobile device 170 from the medical image provision system 160, and may control the display unit 340 so that the received medical image is displayed.

Furthermore, the image processing unit 316 may receive medical images to be output to the respective slave mobile devices 181, 182 and 183 from the medical image provision system 160, and may control the communication unit 320 so that the medical images to be output to the slave mobile devices 181, 182 and 183 are transmitted to the slave mobile devices 181, 182 and 183 via the communication unit 320.

If the master mobile device 170 does not relay communication between the medical image provision system 160 and the slave mobile devices 181, 182 and 183, the device interface unit 318 may detect only information input by a user via the user interface unit 350, and may provide the detected information to be transmitted to the medical image provision system 160 via the communication unit 320.

If the master mobile device 170 relays communication between the medical image provision system 160 and the slave mobile devices 181, 182 and 183, the device interface unit 318 may provide information input by a user via the user interface unit 350 or information about the input of the slave mobile devices 181, 182 and 183 via the communication unit 320 to be transmitted to the medical image provision system 160 via the communication unit 320.

The control unit 310 may control the overall operation of the master mobile device 170. Furthermore, the control unit 310 may perform the functions of the device information collection unit 312, the arrangement designation unit 314, the image processing unit 316, and the device interface unit 318. The control unit 310, the device information collection unit 312, the arrangement designation unit 314, the image processing unit 316, and the device interface unit 318 have been illustrated as being separate only in order to simply describe and explain the functions. Accordingly, the control unit 310, the device information collection unit 312, the arrangement designation unit 314, the image processing unit 316 and the device interface unit 318 may be implemented in one or more processors in the master mobile device 170. Alternatively, the control unit 310 may include at least one processor configured to perform part of the functions of the device information collection unit 312, the arrangement designation unit 314, the image processing unit 316 and the device interface unit 318.

Figure 4:
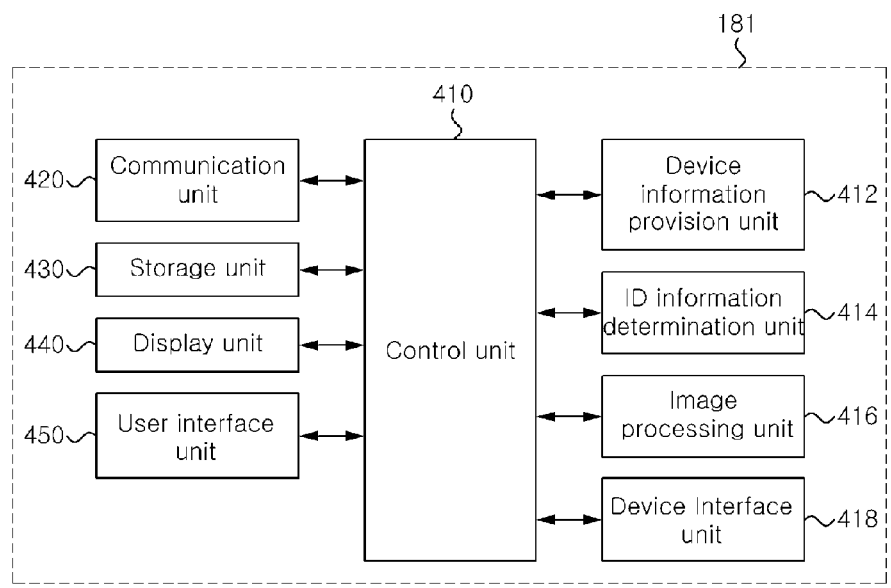
FIG. 4 is a diagram illustrating the configuration of a slave mobile device according to an embodiment of the present invention.

FIG. 4 is a diagram illustrating the configuration of the slave mobile device according to an embodiment of the present invention.

Referring to FIG. 4, the slave mobile device (e.g., 181) may include a control unit 410, a device information provision unit 412, an ID information determination unit 414, an image processing unit 416, an device interface unit 418, a communication unit 420, a storage unit 430, a display unit 440, and an user interface unit 450. The control unit 410, the device information provision unit 412, the ID information determination unit 414, the image processing unit 416, and the device interface unit 418 may be implemented as at least one processor in the slave mobile device 181.

The communication unit 420 is a communication interface device including a receiver and a transmitter. The communication unit 320 is connected to the master mobile device 170 or the medical image provision system 160 through wireless communication, and is configured to send and receive data to and from the master mobile device 170 or the medical image provision system 160. In this case, the communication unit 420 may use short-distance communication. Available short-distance wireless communication may include Wi-Fi, Bluetooth, near field communication (NFC), and infrared communication. Among them, Bluetooth or Wi-Fi may be preferably used because they are most widely used in mobile terminals and provide the widest coverage.

The storage unit 430 may store an operating system operative to control the overall operation of the slave mobile device 181, an application program, and data (e.g., telephone numbers, SMS messages, compressed image files, and moving images), and may also store the device information of the slave mobile device 181 and information about the ID of the slave mobile device 181, which is received via the communication unit 420, according to an embodiment of the present invention.

The display unit 440 may display information input by a user or information provided to the various menus of the slave mobile device 181, information about the ID of the slave mobile device 181, medical images, and medical information. The display unit 440 may be formed of an LCD, OLEDs, or AMOLEDs, but is not limited thereto. If the display unit 440 is formed of a touch screen, the display unit 440 may function as the user interface unit 450.

The user interface unit 450 receives input from the user of the slave mobile device 181, and provides the input to the control unit 410. In particular, the user interface unit 450 may receive a change of a medical image or a change of medical information. Various input devices may be used as the user interface unit 450. For example, the user interface unit 450 may include numerical keys 0~9, text keys, navigator keys, and a plurality of function keys. The user interface unit 450 may be formed of a keypad configured to provide key input data, corresponding to a key pressed by a user, to the control unit 410, or may be formed of a touch screen including a touch sensor for detecting a touch location on a display screen as input.

The device information provision unit 412 may be a sub-module of a processor in the slave mobile device 181. When a request for the device information of the slave mobile device 181 is received from the master mobile device 170 via the communication unit 420, the device information provision unit 412 control the communication unit 420 so that the device information of the slave mobile device 181 stored in the storage unit 430 is transmitted to the master mobile device 170 via the communication unit 420.

The ID information determination unit 414 may be another sub-module of the processor in the slave mobile device 181 and may receive information about the ID of the slave mobile device 181 or recommended arrangement information via the communication unit 420 from the master mobile device 170 or the medical image provision system 160.

When recommended arrangement information is received, the ID information determination unit 414 checks information about the ID of the slave mobile device 181 included in the recommended arrangement information.

The image processing unit 416 may be another sub-module of the processor in the slave mobile device 181. Once the arrangement of the mobile devices 170, 181, 182 and 183 has been configured, the image processing unit 416 may provide to the display unit 440 the ID information checked by the ID information determination unit 414 to be displayed on the display unit 440.

Thereafter, the image processing unit 416 may receive a medical image to be output to the slave mobile device 181 via the communication unit 420 from the master mobile device 170 or the medical image provision system 160, and may provide to the display unit 440 the received medical image to be displayed on the display unit 440.

In this case, the type of received medical image may include a medical image captured using photographing equipment, such as CT equipment or MRI equipment, a 3D medical image rendered in a 3D way, a medical image displaying an affected part, a coronal medical image, a sagittal medical image, and a horizontal medical image. The received medical image may include medical information in addition to a medical image. In this case, the medical information may include a worklist, a medical record, patient information, and a medical plan.

If the master mobile device 170 does not relay communication between the medical image provision system 160 and the slave mobile devices 181, 182 and 183, the device interface unit 418 may detect information input by a user via the user interface unit 450, and may provide the detected information to be transmitted to the medical image provision system 160 via the communication unit 420.

If the master mobile device 170 relays communication between the medical image provision system 160 and the slave mobile devices 181, 182 and 183, the device interface unit 418 may provide information input by a user via the user interface unit 450 to be transmitted to the master mobile device 170 via the communication unit 320.

The control unit 410 may control the overall operation of the slave mobile device 181. Furthermore, the control unit 410 may perform the functions of the device information provision unit 412, the ID information determination unit 414, the image processing unit 416 and the device interface unit 418. The control unit 410, the device information provision unit 412, the ID information determination unit 414, the image processing unit 416 and the device interface unit 418 have been illustrated as being separate only in order to simply explain and describe the functions. Accordingly, control unit 410, the device information provision unit 412, the ID information determination unit 414, the image processing unit 416, and the device interface unit 418 may be implemented in one or more processors in the slave mobile device 181. Alternatively, the control unit 410 may include at least one processor configured to perform part of the functions of the device information provision unit 412, the ID information determination unit 414, the image processing unit 416, and the device interface unit 418.

A method of displaying a medical image using multiple mobile devices according to an embodiment of the present invention is described in detail below with reference to drawings.

Figure 5:
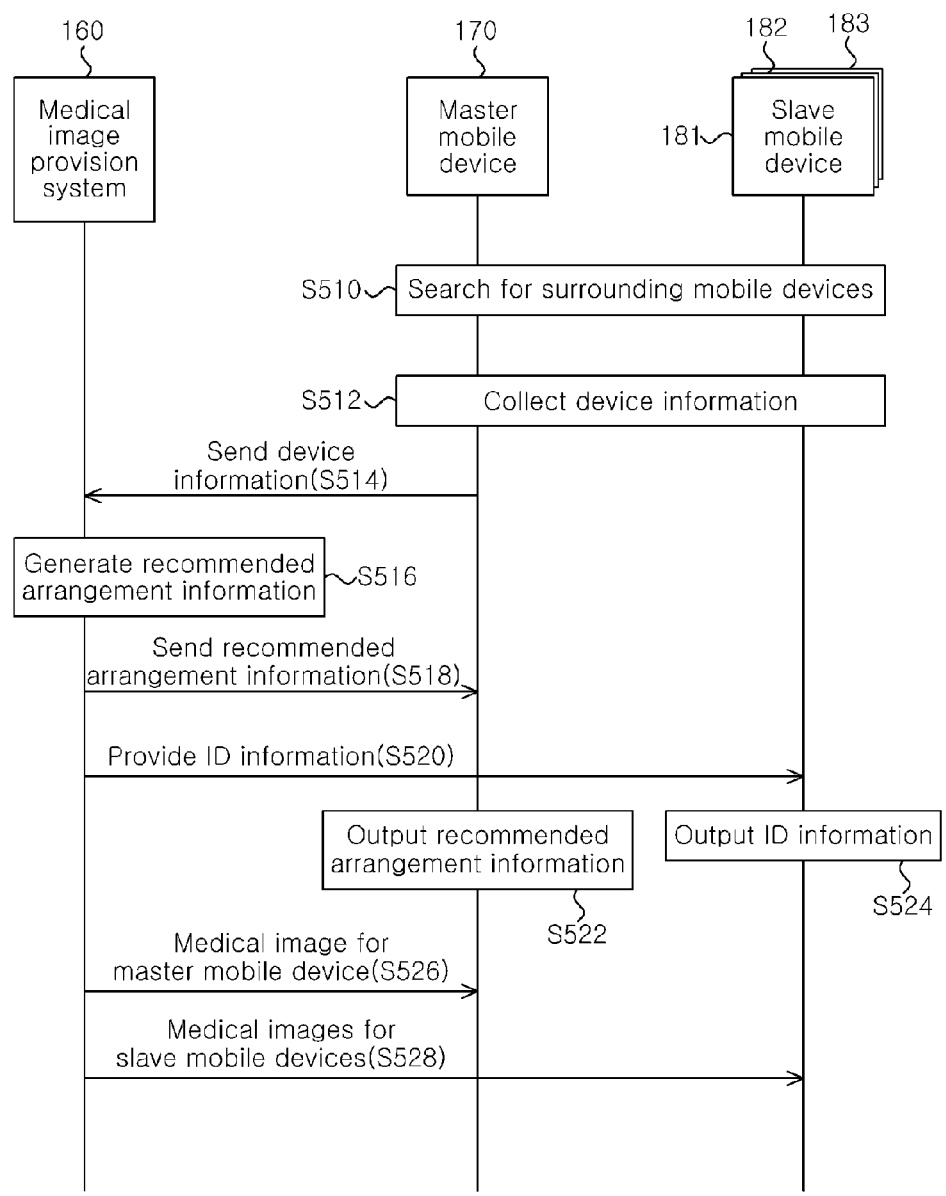
FIG. 5 is a flowchart illustrating a process of designating the display of a medical image using multiple mobile devices according to an embodiment of the present invention.

FIG. 5 is a flowchart illustrating a process of designating the display of a medical image using multiple mobile devices according to an embodiment of the present invention.

Referring to FIG. 5, the master mobile device 170 searches for surrounding slave mobile devices (e.g., 181, 182 and 183) capable of communication at step S510. For example, if Bluetooth communication is used, the master mobile device 170 may search for the slave mobile devices 181, 182 and 183 through pairing for communication connection.

The master mobile device 170 collects the device information of the respective retrieved slave mobile devices 181, 182 and 183 while communicating with the retrieved slave mobile devices 181, 182 and 183 at step S512.

The master mobile device 170 sends its device information and the collected device information to the medical image provision system 160 at step S514.

The medical image provision system 160 generates recommended arrangement information, including the type of medical image configured for each of the mobile devices 170, 181, 182 and 183 and the layout arrangement of the configured mobile devices 170, 181, 182 and 183, at step S516.

The medical image provision system 160 sends the recommended arrangement information to the master mobile device 170 at step S518, and sends information about the IDs of the respective slave mobile devices 181, 182 and 183 to the slave mobile devices 181, 182 and 183 at step S520.

The master mobile device 170 outputs the recommended arrangement information for the master mobile device 170 and the retrieved slave mobile devices 181, 182 and 183, received from the medical image provision system 160, at step S522.

The slave mobile devices 181, 182 and 183 output the pieces of the ID information received from the medical image provision system 160 at step S524.

The medical image provision system 160 sends a medical image to be output by the master mobile device 170 to the master mobile device 170 at step S526, and sends medical images to be output by the respective slave mobile devices 181, 182 and 183 to the slave mobile devices 181, 182 and 183 at step S528.

Figure 6:
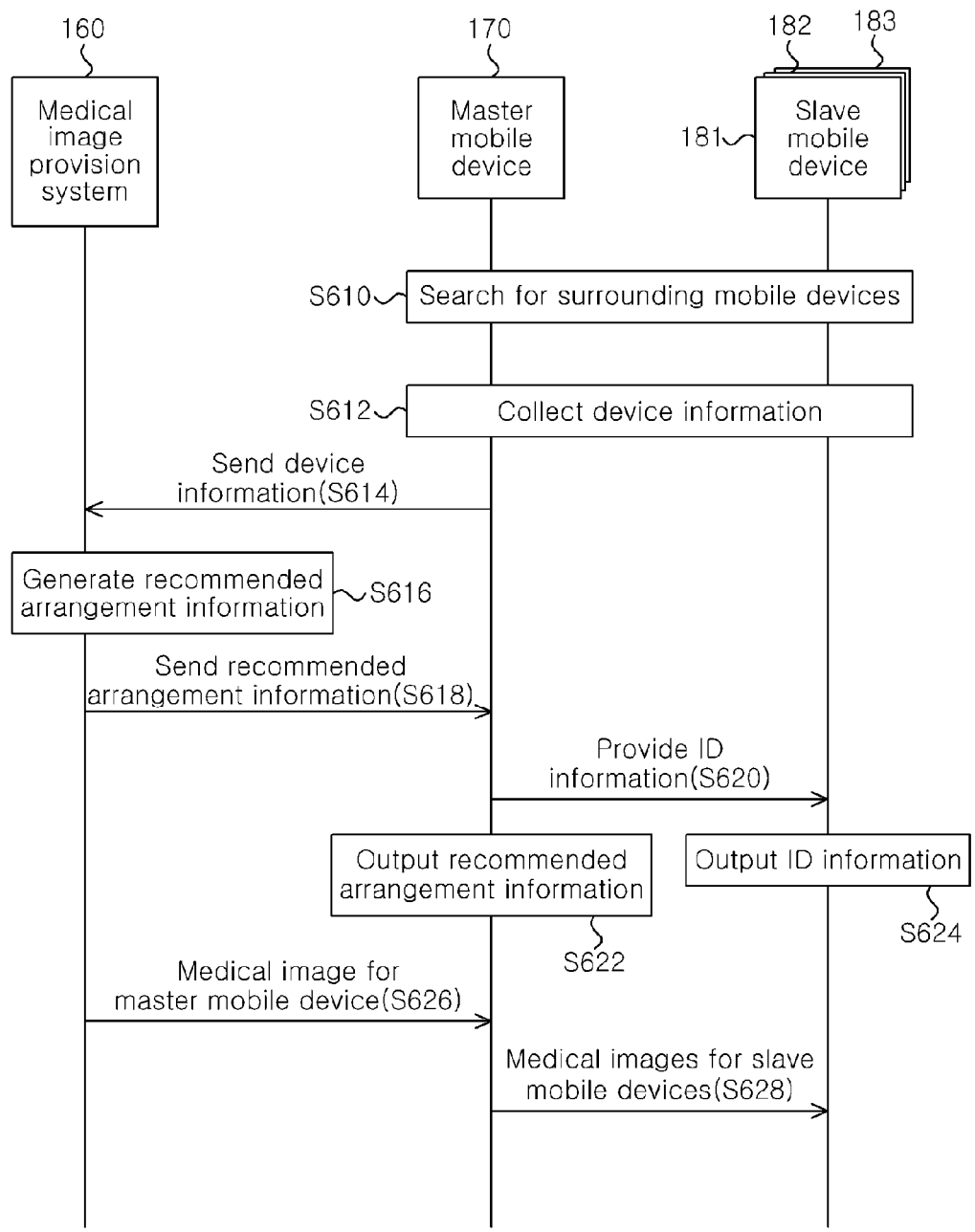
FIG. 6 is a flowchart illustrating a process of designating the display of a medical image using multiple mobile devices according to another embodiment of the present invention.

FIG. 6 is a flowchart illustrating a process of designating the display of a medical image using multiple mobile devices according to another embodiment of the present invention.

Referring to FIG. 6, the master mobile device 170 searches for surrounding slave mobile devices (e.g., 181, 182 and 183) capable of communication at step S610. For example, if Bluetooth communication is used, the master mobile device 170 may search for the slave mobile devices 181, 182 and 183 through pairing for communication connection.

The master mobile device 170 collects the device information of the respective retrieved slave mobile devices 181, 182 and 183 while communicating with the retrieved slave mobile devices 181, 182 and 183 at step S612.

The master mobile device 170 sends its device information and the collected device information to the medical image provision system 160 at step S614.

The medical image provision system 160 generates recommended arrangement information, including the type of medical image configured for each of the mobile devices 170, 181, 182 and 183 and the layout arrangement of the configured mobile devices 170, 181, 182 and 183, at step S616.

The medical image provision system 160 sends the recommended arrangement information to the master mobile device 170 at step S618.

The master mobile device 170 receives the recommended arrangement information for the master mobile device 170 and the retrieved slave mobile devices 181, 182 and 183 from the medical image provision system 160 at step S618, and sends information about the IDs of the respective slave mobile devices 181, 182 and 183 to the slave mobile devices 181, 182 and 183 at step S560.

The master mobile device 170 outputs the received recommended arrangement information at step S622.

The slave mobile devices 181, 182 and 183 receive the information about their ID from the master mobile device 170 at step S620, and output the received ID information at step S624.

The medical image provision system 160 sends all medical images to be output by the respective mobile devices to the master mobile device 170 at step S626.

The master mobile device 170 receives the medical images to be output by the master mobile device 170 and the slave mobile devices 181, 182 and 183 at step S626, and sends medical images that belong to the received medical images and that are to be output by the slave mobile devices 181, 182 and 183 to the slave mobile devices 181, 182 and 183 at step S628.

Figure 7:
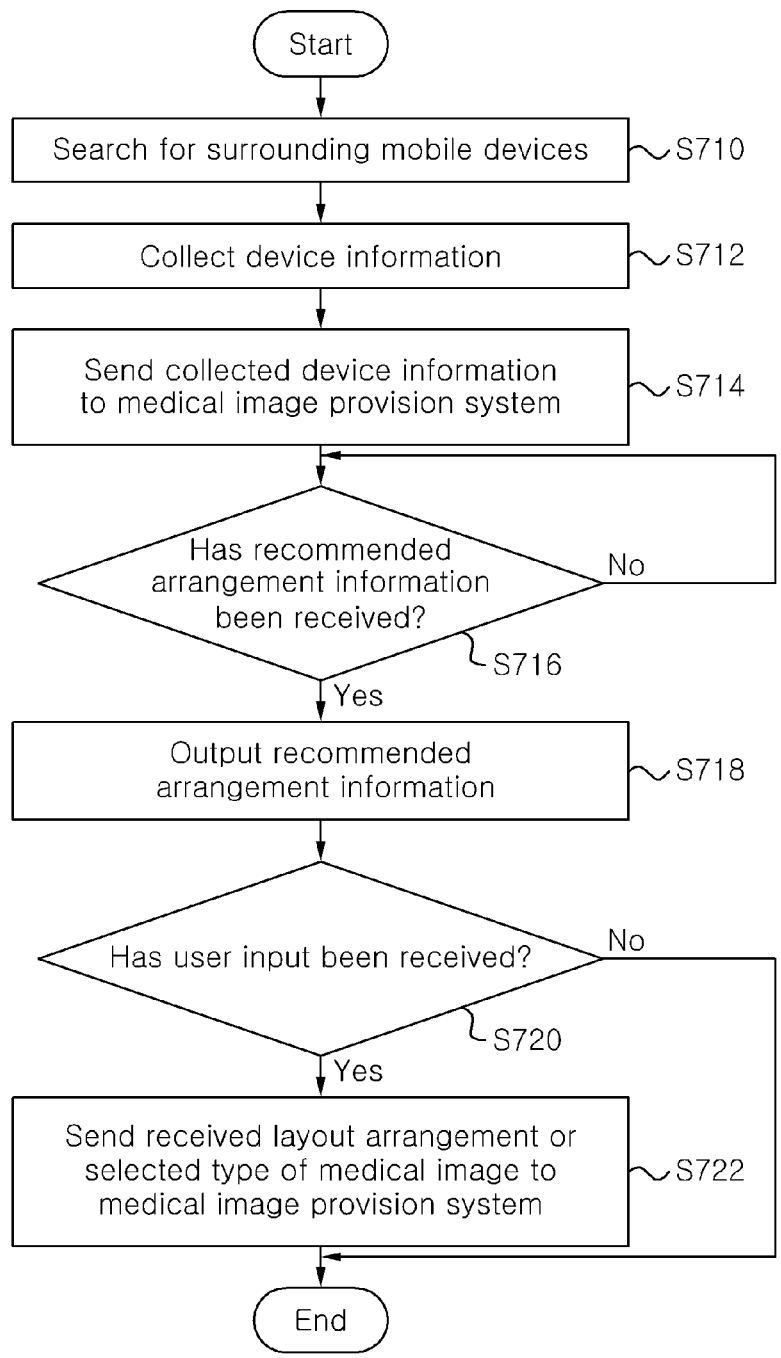
FIG. 7 is a flowchart illustrating a process in which a master mobile device configures the display of a medical image according to an embodiment of the present invention.

FIG. 7 is a flowchart illustrating a process in which the master mobile device configures the display of a medical image according to an embodiment of the present invention.

Referring to FIG. 7, the master mobile device 170 searches for surrounding slave mobile devices (e.g., 181, 182 and 183) capable of communication at step S710.

The master mobile device 170 collects the device information of the respective retrieved slave mobile devices 181, 182 and 183 while communicating with the retrieved slave mobile devices 181, 182 and 183 at step S712.

The master mobile device 170 sends its device information and the collected device information of the slave mobile devices 181, 182 and 183 to the medical image provision system 160 at step S714.

Furthermore, once recommended arrangement information for the master mobile device 170 and the retrieved slave mobile devices 181, 182 and 183 has been received from the medical image provision system 160 at step S716, the master mobile device 170 outputs the recommended arrangement information at step S718.

In this case, the recommended arrangement information may be configured to include information about the IDs of the master mobile device 170 and the retrieved slave mobile devices 181, 182 and 183, arrangement information about the layout arrangement of the master mobile device 170 and the retrieved slave mobile devices 181, 182 and 183, and information about the type of medical image to be output by each of the master mobile device 170 and the retrieved slave mobile devices 181, 182 and 183.

Alternatively, if a single medical image is split and displayed on the master mobile device 170 and the retrieved slave mobile devices 181, 182 and 183, the recommended arrangement information may be configured to include information about the IDs of the master mobile device 170 and the retrieved slave mobile devices 181, 182 and 183, arrangement information about the layout arrangement of the master mobile device 170 and the retrieved slave mobile devices 181, 182 and 183, and information about the regions of the medical image to be output by the master mobile device 170 and the retrieved slave mobile devices 181, 182 and 183, respectively.

Once the layout arrangement of the master mobile device 170 and the retrieved slave mobile devices 181, 182 and 183 has been received from a user or the type of medical image to be output by each of the master mobile device 170 and the retrieved slave mobile devices 181, 182 and 183 has been selected by the user at step S720, the master mobile device 170 sends the received layout arrangement or the type of selected image to the medical image provision system 160 at step S722.

Figure 8:
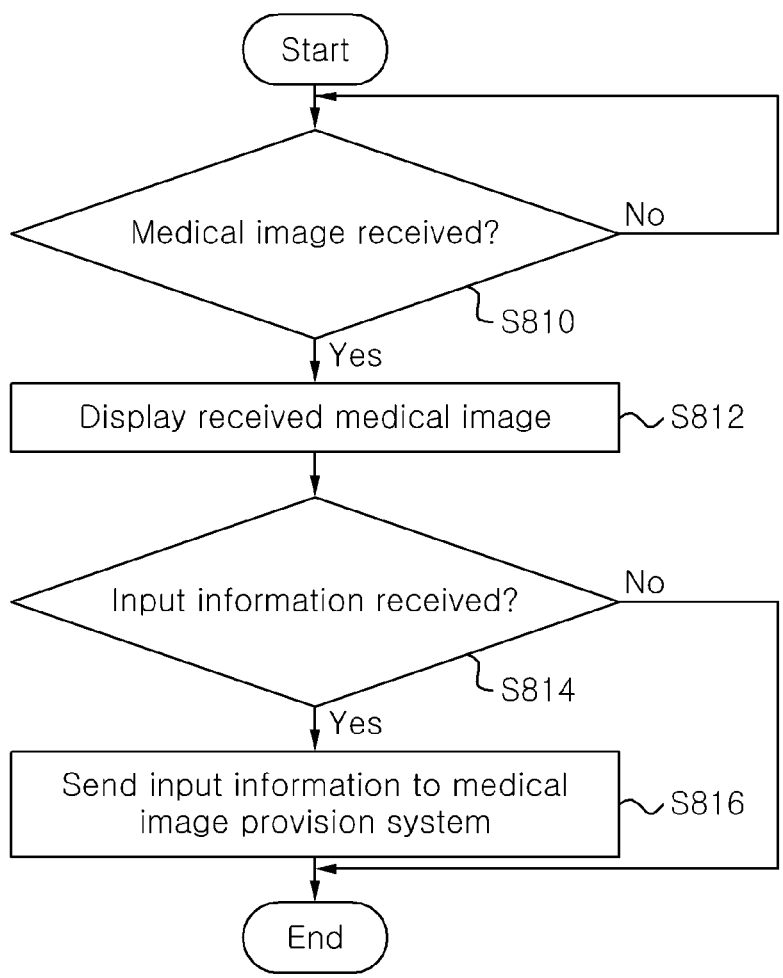
FIG. 8 is a flowchart illustrating an example in which the master mobile device provides a medical image after a configuration has been completed according to an embodiment of the present invention.

FIG. 8 is a flowchart illustrating an example in which the master mobile device provides a medical image after the master mobile device has been configured according to an embodiment of the present invention.

Referring to FIG. 8, once a medical image to be output to the master mobile device 170 has been received from the medical image provision system 160 at step S810, the master mobile device 170 displays the received medical image at step S812.

Furthermore, once information input by a user has been received at step S814, the master mobile device 170 sends the input information to the medical image provision system 160 at step S816.

Figure 9:
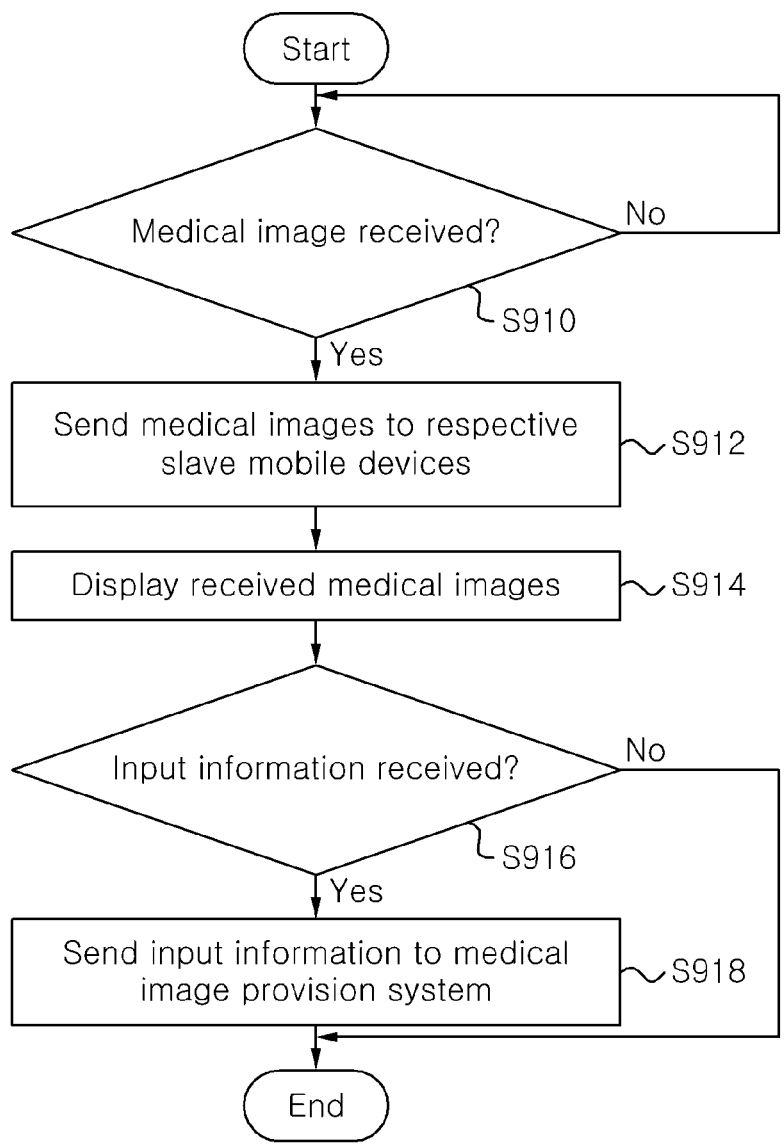
FIG. 9 is a flowchart illustrating another example in which the master mobile device provides a medical image after a configuration has been completed according to an embodiment of the present invention.

FIG. 9 is a flowchart illustrating another example in which the master mobile device provides medical images after the master mobile device has been configured according to an embodiment of the present invention.

Referring to FIG. 9, once medical images to be output to the master mobile device 170 and the slave mobile devices 181, 182 and 183 have been received from the medical image provision system 160 at step S910, the master mobile device 170 sends medical images that belong to the received medical images and that are to be output by the slave mobile devices 181, 182 and 183 to the slave mobile devices 181, 182 and 183 at step S912.

The master mobile device 170 displays the received medical image at step S914.

Furthermore, once information input by a user has been received from the master mobile device 170 or the slave mobile devices 181, 182 and 183 at step S916, the master mobile device 170 sends the received input information to the medical image provision system 160 at step S918.

Figure 10:
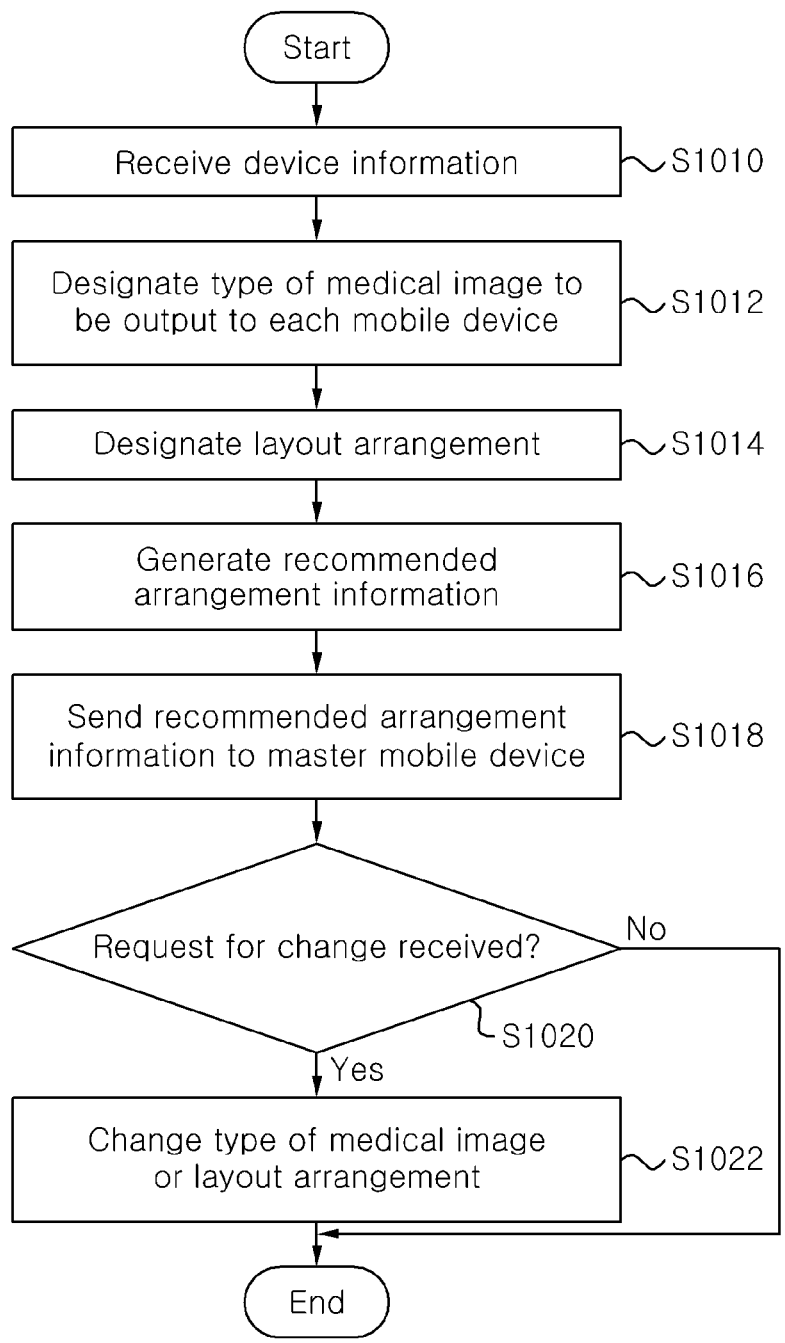
FIG. 10 is a flowchart illustrating a process in which the medical image provision system configures the display of medical image according to an embodiment of the present invention.

FIG. 10 is a flowchart illustrating a process in which the medical image provision apparatus configures the display of medical image according to an embodiment of the present invention.

Referring to FIG. 10, the medical image provision system 160 receives the device information of the master mobile device 170 and the slave mobile devices 181, 182 and 183 from the master mobile device 170 at step S1010.

The medical image provision system 160 designates the type of medical image to be output to each of the master mobile device 170 and the slave mobile devices 181, 182 and 183 based on the device information of the master mobile device 170 and the slave mobile devices 181, 182 and 183 at step S1012.

Furthermore, the medical image provision system 160 designates the layout arrangement of the master mobile device 170 and the slave mobile devices 181, 182 and 183 at step S1014.

In this case, one or more of an layout arrangement predetermined by a user, an layout arrangement designated most frequently, and an layout arrangement designated based on a user's role may be set as the layout arrangement.

The medical image provision system 160 generates recommended arrangement information, including the type of medical image designated for each of the master mobile device 170 and the slave mobile devices 181, 182 and 183 and the configured layout arrangement, at step S1016.

The medical image provision system 160 sends the recommended arrangement information to the master mobile device 170 at step S1018.

Once a request for a change of the type of medical image to be output to each of the mobile devices 170, 181, 182 and 183 or a change of the layout arrangement has been received from the master mobile device 170 at step S1020, the medical image provision system 160 changes the type of medical image to be output to each of the mobile devices 170, 181, 182 and 183 or the layout arrangement in response to the request at step S1022.

Figure 11:
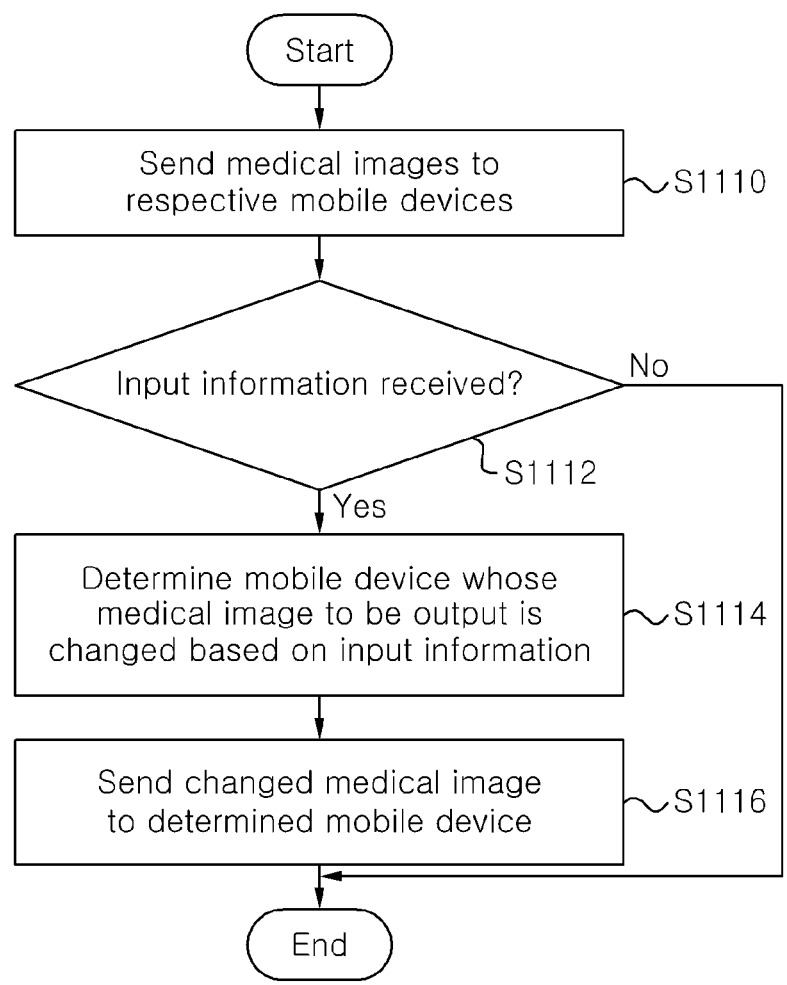
FIG. 11 is a flowchart illustrating a process in which the medical image provision system provides a medical image according to an embodiment of the present invention.

FIG. 11 is a flowchart illustrating a process in which the medical image provision apparatus provides a medical image according to an embodiment of the present invention.

Referring to FIG. 11, the medical image provision system 160 sends medical images to be output by the master mobile device 170 and the slave mobile devices 181, 182 and 183 to the master mobile device 170 and the slave mobile devices 181, 182 and 183 at step S1110.

In this case, the medical image provision system 160 sends all the medical images to be output by the respective mobile devices to the master mobile device 170 so that medical images that belong to the medical images and that are to be output by the slave mobile devices 181, 182 and 183 are transferred to the slave mobile devices 181, 182 and 183 via the master mobile device 170.

Furthermore, once information input by a user has been received from the master mobile device 170 or the slave mobile devices 181, 182 and 183 at step S1112, the medical image provision system 160 determines a mobile device whose medical image to be output is changed based on the input information at step S1114.

In this case, the input information may be received from each of the mobile devices 170, 181, 182 and 183 or from all the mobile devices 170, 181, 182 and 183 via the master mobile device 170.

The medical image provision system 160 sends a corresponding changed medical image to each of the checked mobile device at step S1116. In this case, the medical image provision system 160 may send corresponding changed medical images to the respective checked mobile devices or may send all the changed medical images to the master mobile device 170 so that the changed medical images are transferred to the respective checked mobile devices.

Figure 12:
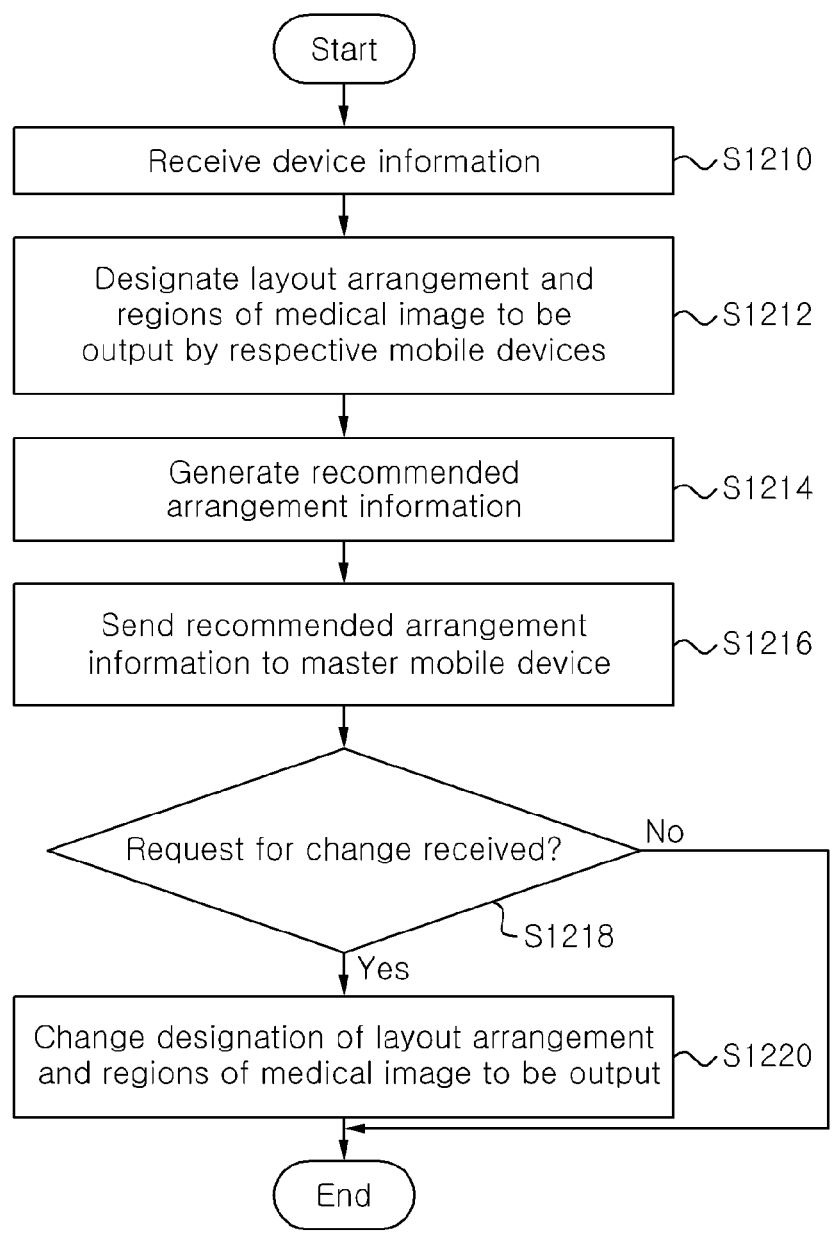
FIG. 12 is a flowchart illustrating a process in which the medical image provision system configures the display of a medical image according to another embodiment of the present invention.

FIG. 12 is a flowchart illustrating a process in which the medical image provision apparatus configures the display of medical images according to another embodiment of the present invention.

Referring to FIG. 12, the medical image provision system 160 receives the device information of the master mobile device 170 and the slave mobile devices 181, 182 and 183 from the master mobile device 170 at step S1210.

If a single medical image is split and displayed, the medical image provision system 160 designates the layout arrangement of the master mobile device 170 and retrieved slave mobile devices (e.g., 181, 182 and 183) and the regions of the medical image to be output by the master mobile device 170 and the retrieved slave mobile devices 181, 182 and 183 based on the device information of the master mobile device 170 and the retrieved slave mobile devices 181, 182 and 183 at step S1212.

The medical image provision system 160 generates recommended arrangement information, including the configured layout arrangement and information about the regions of the medical image configured for the master mobile device 170 and the retrieved slave mobile devices 181, 182 and 183, at step S1214.

The medical image provision system 160 sends the recommended arrangement information to the master mobile device 170 at step S1216.

Furthermore, once a request for a change of a region of the medical image to be output or a change of the layout arrangement has been received from the master mobile device 170 at step S1218, the medical image provision system 160 changes the designation of the region of the medical image or the layout arrangement in response to the request at step S1220.

Figure 13:
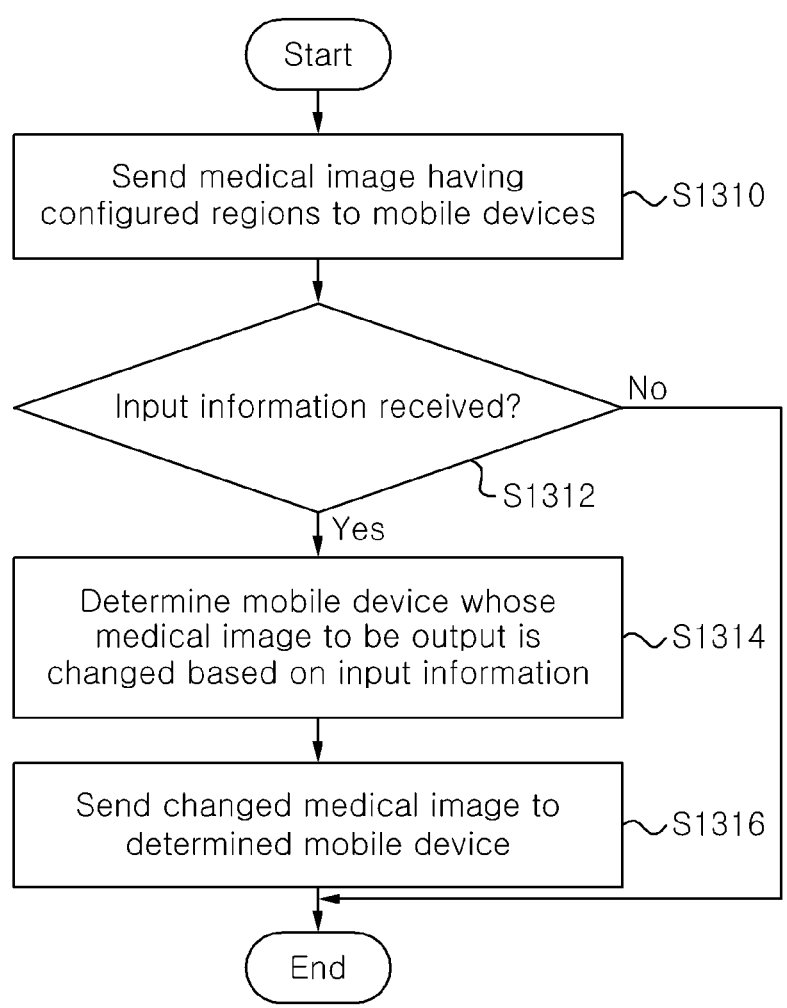
FIG. 13 is a flowchart illustrating a process in which the medical image provision system provides a medical image after a configuration has been completed according to another embodiment of the present invention.

FIG. 13 is a flowchart illustrating a process in which the medical image provision apparatus provides a medical image after a designation has been completed according to another embodiment of the present invention.

Referring to FIG. 13, the medical image provision system 160 sends a medical image whose regions to be output by the master mobile device 170 and the slave mobile devices 181, 182 and 183 have been configured to the master mobile device 170 and the slave mobile devices 181, 182 and 183 at step S1310.

In this case, the medical image provision system 160 may send information about the regions to the respective mobile devices 170, 181, 182 and 183 along with the same medical image, or may send medical images, split for the respective mobile devices, to the respective mobile devices 170, 181, 182 and 183.

Alternatively, the medical image provision system 160 may send both information about the regions of the medical image to be output by the respective mobile devices 170, 181, 182 and 183 and the medical image to the master mobile device 170 so that the information about the regions of the medical image and the medical image are transferred to the slave mobile devices 181, 182 and 183 via the master mobile device 170.

Furthermore, when information input by a user is received from the master mobile device 170 or the slave mobile devices 181, 182 and 183 at step S1312, the medical image provision system 160 determines a mobile device whose medical image is changed based on the input information at step S1314. In this case, the input information may be received from each of the mobile devices 170, 181, 182 and 183 or from all the mobile devices 170, 181, 182 and 183 via the master mobile device 170.

Furthermore, the medical image provision system 160 sends a corresponding changed medical image to the determined mobile device at step S1316. In this case, a corresponding changed medical image may be transmitted to each of the determined mobile devices, or all the changed medical images may be transmitted to the master mobile device 170 so that the changed medical images are transferred to the respective checked mobile devices.

Figure 14:
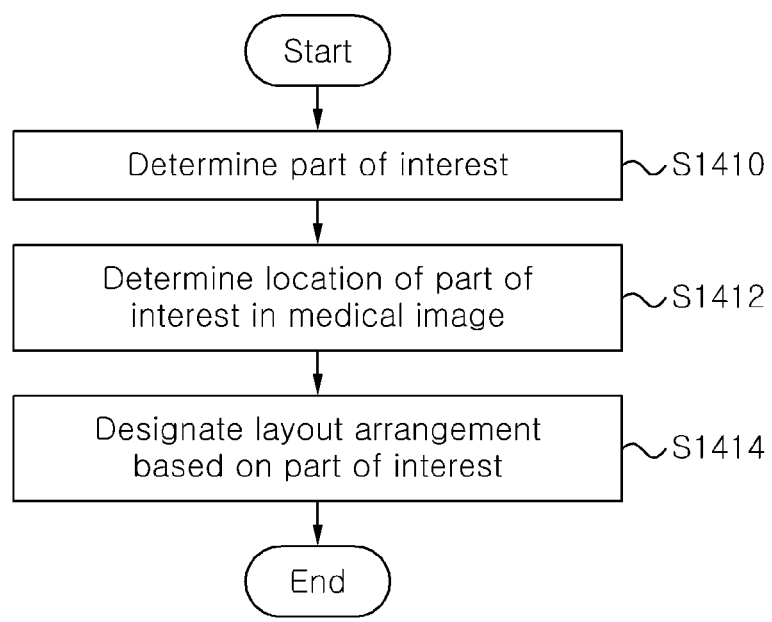
FIG. 14 is a flowchart illustrating a process in which the medical image provision system configures an layout arrangement according to another embodiment of the present invention.

FIG. 14 is a flowchart illustrating a process in which the medical image provision apparatus configures an layout arrangement according to another embodiment of the present invention.

Referring to FIG. 14, the medical image provision system 160 determines a part of interest in annotation, marking, or a header included in a medical image at step S1410.

The medical image provision system 160 determines the location of the part of interest in the medical image at step S141.

Furthermore, the medical image provision system 160 designates an layout arrangement so that the part of interest is placed in a mobile device having the highest resolution or a mobile device having the largest display at step S1414.

As described above, according to the present invention, when the medical image provision system receives the device information of mobile devices, the medical image provision system can designate the type of medical image to be output to each of the mobile devices based on the device information, can designate the layout arrangement of the mobile devices, can generate recommended arrangement information including the type of configured image and the configured layout arrangement, and can send the recommended arrangement information to the master mobile device so that the arrangement of the mobile devices can be designated. Accordingly, one or more medical images can be effectively displayed via multiple mobile devices.

The method of displaying a medical image using multiple mobile devices according to an embodiment of the present invention may be implemented in the form of program instructions and stored in a computer-readable medium. The computer-readable medium may store the program instructions, data files, and data structures solely or in combination. The program instructions recorded on the medium may have been specially designed and implemented for the present invention or may have been known to those skilled in the computer software field and be used. Examples of the computer-readable medium include all types of hardware devices specially configured to store and execute the program instructions, such as magnetic media including a hard disk, a floppy disk, and a magnetic tape, optical media including compact disc (CD) ROM and digital video disc (DVD) ROM, magneto-optical media including a floptical disk, RAM, and flash memory. Examples of the program instructions include machine code, such as one produced by a compiler, and high-level language code executable by computers using an interpreter. The hardware device may be configured with one or more software modules for performing the operation of the present invention, and the vice versa.

Furthermore, the method of displaying a medical image using multiple mobile devices according to an embodiment of the present invention may be implemented in the form of program instructions that may be executed via various computer means, and may be loaded onto system memory and executed by a processor in the form of program instructions.

Although the preferred embodiments of the present invention have been disclosed for illustrative purposes, those skilled in the art will appreciate that various modifications, additions and substitutions are possible without departing from the scope and spirit of the invention as disclosed in the accompanying claims.

What is claimed is:

1. A mobile device for displaying a medical image, comprising:
   a communication unit configured to wirelessly communicate with surrounding mobile devices and a medical image provision system;
   a processor configured to:
      search for surrounding slave mobile devices that are to operate as slaves via the communication unit;
      collect device information of each of the retrieved slave mobile devices while communicating with the retrieved slave mobile devices;
      control the communication unit to transmit device information of the mobile device and the collected device information to the medical image provision system; arrangement designation
      receive recommended arrangement information for the mobile device and the retrieved slave mobile devices from the medical image provision system; and
      output the recommended arrangement information,
   wherein the recommended arrangement information comprises:
      information about identities (IDs) of the mobile device and the retrieved slave mobile devices,
      arrangement information about a layout arrangement of the mobile device and the retrieved slave mobile devices, and
      information about a type of medical image to be output by each of the mobile device and the retrieved slave mobile devices.

2. The mobile device of claim 1, wherein the device information comprises one or more of:
   a resolution of a display included in each of the mobile devices, a size of the display screen, a contrast ratio of the display screen, a response speed of the display screen, information about whether or not the display screen is capable of outputting a three-dimensional (3D) image, a size of the mobile device, a processing speed of the mobile device, and a remaining storage space of the mobile device.

3. The mobile device of claim 1, wherein after outputting the recommended arrangement information, the processor, once the layout arrangement of the mobile device and the retrieved slave mobile devices has been received from a user or a type of medical image to be output to each of the mobile device and the retrieved slave mobile devices has been selected by the user, provide the received layout arrangement or the type of selected image to be transmitted to the medical image provision system via the communication unit.

4. The mobile device of claim 1, the processor is further configured to:
   receive a medical image to be displayed on the mobile device from the medical image provision system.

5. The mobile device of claim 1, the processor is further configured to:

receive medical images to be output to the respective slave mobile devices from the medical image provision system; and control the communication unit to transmit the received medical images to the slave mobile devices via the communication unit.

6. The mobile device of claim 1, the processor is further configured to:

receive input information from each of the slave mobile devices; and control the communication unit to transmit the input information to the medical image provision system via the communication unit.

7. The mobile device of claim 1, wherein the recommended arrangement information, if a single medical image is split and displayed on the mobile device and the retrieved slave mobile devices, comprises information about IDs of the mobile device and the retrieved slave mobile devices, arrangement information about a layout arrangement of the mobile device and the retrieved slave mobile devices, and information about regions of the medical image to be output by the mobile device and the retrieved slave mobile devices.

8. The mobile device of claim 7, wherein the processor, if a layout arrangement of the mobile device and the retrieved slave mobile devices or a change of the region of the medical image to be output by each of the mobile device and the retrieved slave mobile devices is received from a user after outputting the recommended arrangement information, controls the communication unit to transmit the received layout arrangement or the changed region of the medical image to the medical image provision system via the communication unit.

9. A method of displaying a medical image in a mobile device of a system for displaying medical image, the method comprising:

searching, by a processor within the mobile device, for surrounding slave mobile devices capable of communication;

collecting, by the processor within the mobile device, device information of each of the retrieved slave mobile devices while communicating with the retrieved slave mobile devices;

sending, by the processor within the mobile device, device information of the mobile device and the collected device information to a medical image provision system;

receiving, by the processor within the mobile device, recommended arrangement information for the mobile device and the retrieved slave mobile devices from the medical image provision system; and outputting, by the processor within the mobile device, the recommended arrangement information, wherein the recommended arrangement information comprises:

information about identities (IDs) of the mobile device and the retrieved slave mobile devices, arrangement information about a layout arrangement of the mobile device and the retrieved slave mobile devices, and information about a type of medical image to be output by each of the mobile device and the retrieved slave mobile devices.

10. The method of claim 9, wherein the recommended arrangement information, if a single medical image is split and displayed on the mobile device and the retrieved slave mobile devices, comprises information about IDs of the mobile device and the retrieved slave mobile devices, arrangement information about a layout arrangement of the mobile device and the retrieved slave mobile devices, and information about regions of the medical image to be output by the mobile device and the retrieved slave mobile devices.

* * * * *